United States Patent
Corson et al.

(10) Patent No.: US 7,437,249 B2
(45) Date of Patent: Oct. 14, 2008

(54) METHODS AND SYSTEMS FOR DETRENDING SIGNAL INTENSITY DATA FROM CHEMICAL ARRAYS

(75) Inventors: John Frederick Corson, Mountain View, CA (US); Jayati Ghosh, Sunnyvale, CA (US); Svetlana Shchegrova, Campbell, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 11/479,269

(22) Filed: Jun. 30, 2006

(65) Prior Publication Data

US 2008/0004824 A1 Jan. 3, 2008

(51) Int. Cl.
*G06F 19/00* (2006.01)
*G01N 33/50* (2006.01)

(52) U.S. Cl. ............................ 702/32; 702/30; 702/19; 702/190

(58) Field of Classification Search ............. 702/30–32, 702/189–191, 194–197, 199; 708/300, 303
See application file for complete search history.

(56) References Cited

U.S. PATENT DOCUMENTS

| | | | |
|---|---|---|---|
| 4,700,319 A * | 10/1987 | Steiner | ........................ 708/521 |
| 6,132,969 A | 10/2000 | Stoughton et al. | |
| 6,171,797 B1 | 1/2001 | Perbost | |
| 6,180,351 B1 | 1/2001 | Cattell | |
| 6,221,583 B1 | 4/2001 | Kayyem et al. | |
| 6,222,664 B1 | 4/2001 | Dorsel et al. | |
| 6,232,072 B1 | 5/2001 | Fisher | |
| 6,242,266 B1 | 6/2001 | Schleifer et al. | |
| 6,251,685 B1 | 6/2001 | Dorsel et al. | |
| 6,320,196 B1 | 11/2001 | Dorsel et al. | |
| 6,323,043 B1 | 11/2001 | Caren et al. | |
| 6,351,712 B1 | 2/2002 | Stoughton et al. | |
| 6,355,921 B1 | 3/2002 | Staton et al. | |
| 6,371,370 B2 | 4/2002 | Sadler et al. | |
| 6,406,849 B1 | 6/2002 | Dorsel et al. | |
| 6,410,243 B1 | 6/2002 | Wyrick et al. | |
| 6,486,457 B1 | 11/2002 | Dorsel et al. | |
| 6,518,556 B2 | 2/2003 | Staton et al. | |
| 6,713,257 B2 | 3/2004 | Shoemaker et al. | |
| 2001/0018183 A1* | 8/2001 | Bao et al. | ........................ 435/6 |
| 2003/0093225 A1* | 5/2003 | Fathallah-Shaykh | ......... 702/19 |
| 2003/0186310 A1 | 10/2003 | Kincard et al. | |
| 2003/0226098 A1 | 12/2003 | Weng | |

(Continued)

FOREIGN PATENT DOCUMENTS

WO   WO 93/18186   9/1993

OTHER PUBLICATIONS

Colantuoni et al., SNOMAD (Standardization and NOrmalization of Microarray Data): web-accessible gene expression data analysis. vol. 18 No. 11-2002, pp. 1540-1541.

(Continued)

*Primary Examiner*—Manuel L Barbee

(57) ABSTRACT

Methods, systems and computer readable media for removing trends in signal intensity values from features on a chemical array. Inputted signal values from features on the array are surface fitted to calculate a surface approximation. The surface approximation is normalized and used to de-trend the signal intensity values from the features.

8 Claims, 15 Drawing Sheets

U.S. PATENT DOCUMENTS

| | | | |
|---|---|---|---|
| 2004/0019466 A1 | 1/2004 | Minor et al. | |
| 2004/0229245 A1* | 11/2004 | Bittner et al. | 435/6 |
| 2005/0055193 A1 | 3/2005 | Bondarenko | |
| 2005/0130215 A1 | 6/2005 | Stoughton et al. | |
| 2005/0273268 A1* | 12/2005 | Ghosh et al. | 702/19 |
| 2007/0027637 A1* | 2/2007 | Delenstarr et al. | 702/23 |

OTHER PUBLICATIONS

Parmigiani et al., The Analysis of Gene Expression Data, Springer-Verlag New York, Inc. 2003, pp. 210-229.

www.netlib.org/a/Loess, pp. 1-46, downloaded Jun. 26, 2006.

http://www.itl.nist.gov/div898/handbook/pmd/section1/pmd144. htm, 4.1.4.4. Loess (aka Lowess) pp. 1-4.

Cleveland., Pobust Loccally Weighted Regression and Smoothing Scatterplots. Journal of the American Statistical Association, vol. 74, No. 368, Dec. 1979, pp. 829-836.

Cleveland et al., Locally Weighted Regression: An Approach to Regression Analysis by Local Fitting, Journal of the American Statistical Association, vol. 83, pp. 596-610.).

* cited by examiner

METHODS AND SYSTEMS FOR DETRENDING SIGNAL INTENSITY DATA FROM CHEMICAL ARRAYS

BACKGROUND

Researchers use experimental data obtained from chemical arrays such as microarrays and other similar research test equipment to cure diseases, develop medical treatments, understand biological phenomena, and perform other tasks relating to the analysis of such data. However, the conversion of useful results from this raw data is restricted by physical limitations of, e.g., the nature of the tests and the testing equipment. All biological measurement systems leave their fingerprint on the data they measure, distorting the content of the data, and thereby influencing the results of the desired analysis. Further, the systems for manufacturing and processing the arrays may also induce systematic error. For example, systematic biases can distort microarray analysis results and thus conceal important biological effects sought by the researchers. Biased data can cause a variety of analysis problems, including signal compression, aberrant graphs, and significant distortions in estimates of differential expression. Types of systematic biases include gradient effects, differences in signal response between channels (e.g., for a two channel system), variations in hybridization or sample preparation, pen shifts and subarray variation, and differences in RNA inputs.

Gradient effects or "trends" are those in which there is a pattern of expression signal intensity which corresponds with specific physical locations on the substrate of the array and which may typically be characterized by a smooth change in the expression values from one location on the array to another. This can be caused by variations in array design, manufacturing, and/or hybridization procedures. FIG. 1 shows an example of distortion caused by gradient effects, i.e., a trend, where it can be observed that the signal intensity shows a gradually increasing pattern moving from a first edge 100 (see signals corresponding at 200) to a second edge 102 (corresponding signals 202) of the array. A multiplicative trend is formed when the signal values are multiplied relative to the amount of the true signal level, so that noise is somewhat proportional to the signal level of the feature. One example of a hybridization dome or "hyb dome" is a gradient or trend thought to occur from hybridization processing, where the signal around the perimeter of the array is significantly less than in the middle of the array, because of the impact of the bubbler that circulates the target during hybridization. However, other shapes may result from non-uniform distribution of the target solution as it is mixed or moved during hybridization processing.

De-trending of array data is important not only for validating the data values within an array and for comparison of values within the array (intra-array comparisons), but also for valid comparison of data values between different arrays (interarray comparisons).

Efforts at spatially detrending array data have been made based on statistical processing of log ratio values (signal ratios between first and second channels of a scanner reading the same array, or between two single channel readings from two arrays) or on statistical processing of the signal values themselves. The latter is more difficult since signals may vary over many orders of magnitude and skew the results for some statistical approaches. By working with log ratios between signals, these values vary less and should be centered around a zero ratio value, making it much easier to apply statistical techniques to the data in a reliable fashion.

One such effort was made using a publicly available software package refeffed to as SNOMAD (Standardization and Normalization of Microarray Data), see Colantuoni et al., "SNOMAD (Standardization and Normalization of Micro Array Data): web-accessible gene expression data analysis", Bioinformatics Applications Note, Vol. 18, no. 11, 2002, pp 1540-1541. SNOMAD provides scripts in the R statistical language (r.proiect.org) that are used to generate Z-scores for normalization of variance in the gene expression values of a microarray. In order to correct for variance in gene expression ratios (y-axis) that is unequal across the range of gene expression levels (x-axis), each local mean adjusted log expression ratio (y-value) is standardized to the estimation of the standard deviation of log ratio observations that share similar mean expression levels, as identified by being proximal on the x-axis, as defined by a "span" parameter. This results in the generation of Z-scores in locally estimated standard deviation units, see Parimigiani et al., *The Analysis of Gene Expression Data*, Springer-Verlag New York, Inc. 2003, pp. 210-217. A robust local regression ("loess") is used to calculate the local mean gene expression ratio as it varies across the range of gene expression intensity. The calculation of local mean ratios may not be effective for certain types of trends where signal values vary depending upon the location of a feature on the array (e.g., as in the case of a hyb dome, or other spatially related trends). Further, the scripts provided in SNOMAD are not easily integratable into other analysis software packages, such as feature extraction packages, and are therefore not helpful for automating feature extraction processes.

Thus there is a continuing need for spatial detrending algorithms, techniques and systems that rely upon data obtained from features across diverse locations of an array/substrate to provide more reliable spatial detrending of the signal data when it is affected by location of the features from which the data has been extracted. There is a need for spatial detrending algorithms, techniques and systems for detrending a gradient from any effect, provided that the distortions in signal responsible for the gradient are proportional to the signals at corresponding locations over the gradient.

SUMMARY

The present disclosure provides methods, systems and computer readable media for removing trends in signal intensity values from features on a chemical array, including: inputting signal intensity values from all features on the array after filtering to remove at least one of saturated features, non-uniform features and control features; calculating a log transform of each signal intensity value inputted to provide log signal intensity values; calculating a surface approximation of the log signal intensity values; normalizing surface fit values on the calculated surface approximation in locations corresponding to locations of the features on the array from which signal intensity values were inputted; calculating a reverse log transform of the normalized surface fit values; de-trending the inputted signal intensity values as a function of the normalized surface values in locations corresponding to the locations of the features from which the signal intensity values were inputted; and outputting de-trended signal intensity values.

Methods, systems and computer readable media are provided for removing trends in signal intensity values from features on a chemical array, including: inputting signal intensity values from features on the chemical array, wherein the chemical array contains replicates of features designed to measure a sample; for each feature, averaging signal intensity values for all replicates of that feature; for each feature, normalizing the intensity values of all replicates of that feature to a predetermined intensity value; calculating a surface approximation of the averaged, normalized intensity values versus locations on the array of the replicates from which the averaged, normalized intensity values were calculated; normalizing surface values of the surface approximation at locations corresponding to the locations of features on the array from which signal intensity values were inputted; dividing the signal intensity values from the features by the normalized surface values at locations corresponding to the locations of the features from which the signal intensity values were inputted to provide trend-corrected signal intensity values; and outputting the trend-corrected signal intensity values.

Methods, systems and computer readable media are provided for removing trends in signal intensity values from features on a chemical array, including: inputting signal intensity values from features on the chemical array; segmenting the array into local areas of predetermined dimensions; for each local area, calculating an average signal intensity value from the intensity values inputted of features within that local area; calculating a surface approximation of the average signal intensity values versus locations on the array of the centers of the local areas from which the average signal intensity values were calculated; normalizing surface values of the surface approximation at locations corresponding to the locations of features on the array; dividing the signal intensity values from the features by the normalized surface values at locations corresponding to the locations of the features on the array to provide trend-corrected signal intensity values; and outputting the trend-corrected signal intensity values.

These and other features will become apparent to those persons skilled in the art upon reading the details of the methods, systems and computer readable media as more fully described below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
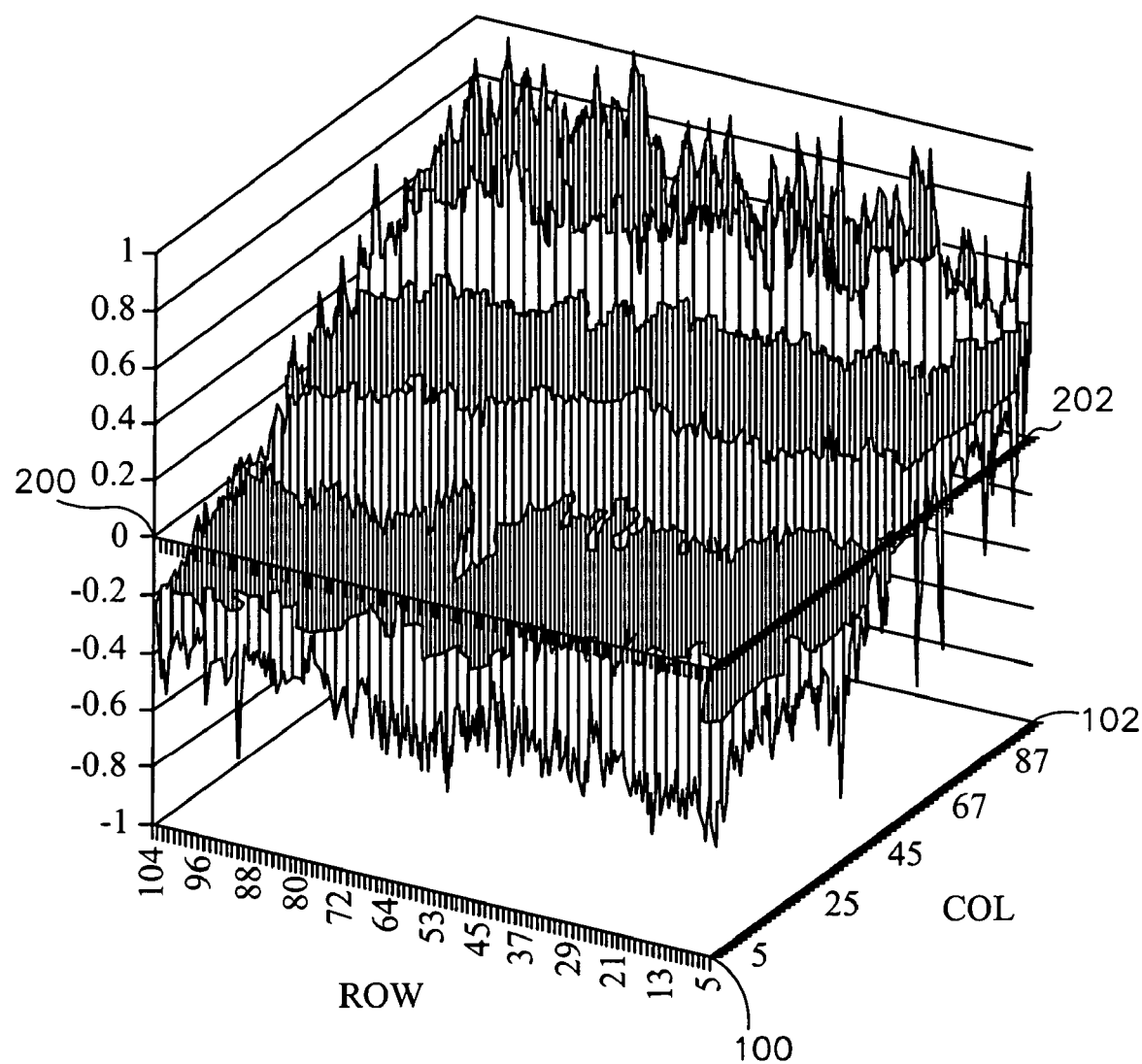
FIG. 1 shows an example of distortion of signal intensities caused by gradient effects.

Before the present methods, systems and computer readable media are described, it is to be understood that this invention is not limited to particular embodiments or examples described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a feature" includes a plurality of such features and reference to "the array" includes reference to one or more arrays and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

A chemical "array", unless a contrary intention appears, includes any one, two or three-dimensional arrangement of addressable regions bearing a particular chemical moiety or moieties (for example, biopolymers such as polynucleotide sequences) associated with that region, where the chemical moiety or moieties are immobilized on the surface in that region. By "immobilized" is meant that the moiety or moieties are stably associated with the substrate surface in the region, such that they do not separate from the region under conditions of using the array, e.g., hybridization and washing and stripping conditions. As is known in the art, the moiety or moieties may be covalently or non-covalently bound to the surface in the region. For example, each region may extend into a third dimension in the case where the substrate is porous while not having any substantial third dimension measurement (thickness) in the case where the substrate is non-porous. An array may contain more than ten, more than one hundred, more than one thousand more than ten thousand features, or even more than one hundred thousand features, in an area of less than 20 cm$^2$ or even less than 10 cm$^2$. For example, features may have widths (that is, diameter, for a round spot) in the range of from about 10 μm to about 1.0 cm. In other embodiments each feature may have a width in the range of about 1.0 μm to about 1.0 mm, such as from about 5.0 μm to about 500 μm, and including from about 10 μm to about 200 μm. Non-round features may have area ranges equivalent to that of circular features with the foregoing width (diameter) ranges. A given feature is made up of chemical moieties, e.g., nucleic acids, that bind to (e.g., hybridize to) the same target (e.g., target nucleic acid), such that a given feature corresponds to a particular target. At least some, or all, of the features are of different compositions (for example, when any repeats of each feature composition are excluded the remaining features may account for at least 5%, 10%, or 20% of the total number of features). Interfeature areas will typically (but not essentially) be present which do not carry any polynucleotide. Such interfeature areas typically will be present where the arrays are formed by processes involving drop deposition of reagents but may not be present when, for example, light directed synthesis fabrication processes are used. It will be appreciated though, that the interfeature areas, when present, could be of various sizes and configurations. An array is "addressable" in that it has multiple regions (sometimes referenced as "features" or "spots" of the array) of different moieties (for example, different polynucleotide sequences) such that a region at a particular predetermined location (an "address") on the array will detect a particular target or class of targets (although a feature may incidentally detect non-targets of that feature). The target for which each feature is specific is, in representative embodiments, known. An array feature is generally homogenous in composition and concentration and the features may be separated by intervening spaces (although arrays without such separation can be fabricated).

In the case of an array, the "target" will be referenced as a moiety in a mobile phase (typically fluid), to be detected by probes ("target probes") which are bound to the substrate at the various regions. However, either of the "target" or "target probes" may be the one which is to be detected by the other (thus, either one could be an unknown mixture of polynucleotides to be detected by binding with the other). "Addressable sets of probes" and analogous terms refer to the multiple regions of different moieties supported by or intended to be supported by the array surface.

The term "sample" as used herein relates to a material or mixture of materials, containing one or more components of interest. Samples include, but are not limited to, samples obtained from an organism or from the environment (e.g., a soil sample, water sample, etc.) and may be directly obtained from a source (e.g., such as a biopsy or from a tumor) or indirectly obtained e.g., after culturing and/or one or more processing steps. In one embodiment, samples are a complex mixture of molecules, e.g., comprising at least about 50 different molecules, at least about 100 different molecules, at least about 200 different molecules, at least about 500 different molecules, at least about 1000 different molecules, at least about 5000 different molecules, at least about 10,000 molecules, etc.

The term "genome" refers to all nucleic acid sequences (coding and non-coding) and elements present in any virus, single cell (prokaryote and eukaryote) or each cell type in a metazoan organism. The term genome also applies to any naturally occurring or induced variation of these sequences that may be present in a mutant or disease variant of any virus or cell type. These sequences include, but are not limited to, those involved in the maintenance, replication, segregation, and higher order structures (e.g. folding and compaction of DNA in chromatin and chromosomes), or other functions, if any, of the nucleic acids as well as all the coding regions and their corresponding regulatory elements needed to produce and maintain each particle, cell or cell type in a given organism.

For example, the human genome consists of approximately $3.0 \times 10^9$ base pairs of DNA organized into distinct chromosomes. The genome of a normal diploid somatic human cell consists of 22 pairs of autosomes (chromosomes 1 to 22) and either chromosomes X and Y (males) or a pair of chromosome Xs (female) for a total of 46 chromosomes. A genome of a cancer cell may contain variable numbers of each chromosome in addition to deletions, rearrangements and amplification of any subchromosomal region or DNA sequence. In certain aspects, a "genome" refers to nuclear nucleic acids, excluding mitochondrial nucleic acids; however, in other aspects, the term does not exclude mitochondrial nucleic acids. In still other aspects, the "mitochondrial genome" is used to refer specifically to nucleic acids found in mitochondrial fractions.

By "genomic source" is meant the initial nucleic acids that are used as the original nucleic acid source from which the probe nucleic acids are produced, e.g., as a template in the nucleic acid amplification and/or labeling protocols.

If a surface-bound polynucleotide or probe "corresponds to" a chromosomal region, the polynucleotide usually contains a sequence of nucleic acids that is unique to that chromosomal region. Accordingly, a surface-bound polynucleotide that corresponds to a particular chromosomal region usually specifically hybridizes to a labeled nucleic acid made from that chromosomal region, relative to labeled nucleic acids made from other chromosomal regions.

An "array layout" or "array characteristics", refers to one or more physical, chemical or biological characteristics of the array, such as positioning of some or all the features within the array and on a substrate, one or more feature dimensions, or some indication of an identity or function (for example, chemical or biological) of a moiety at a given location, or how the array should be handled (for example, conditions under which the array is exposed to a sample, or array reading specifications or controls following sample exposure).

The phrase "oligonucleotide bound to a surface of a solid support" or "probe bound to a solid support" or a "target bound to a solid support" refers to an oligonucleotide or mimetic thereof, e.g., PNA, LNA or UNA molecule that is immobilized on a surface of a solid substrate, where the substrate can have a variety of configurations, e.g., a sheet, bead, particle, slide, wafer, web, fiber, tube, capillary, microfluidic channel or reservoir, or other structure. In certain embodiments, the collections of oligonucleotide elements employed herein are present on a surface of the same planar support, e.g., in the form of an array. It should be understood that the terms "probe" and "target" are relative terms and that a molecule considered as a probe in certain assays may function as a target in other assays.

As used herein, a "test nucleic acid sample" or "test nucleic acids" refer to nucleic acids comprising sequences whose quantity or degree of representation (e.g., copy number) or sequence identity is being assayed. Similarly, "test genomic acids" or a "test genomic sample" refers to genomic nucleic acids comprising sequences whose quantity or degree of representation (e.g., copy number) or sequence identity is being assayed.

As used herein, a "reference nucleic acid sample" or "reference nucleic acids" refers to nucleic acids comprising sequences whose quantity or degree of representation (e.g., copy number) or sequence identity is known. Similarly, "reference genomic acids" or a "reference genomic sample" refers to genomic nucleic acids comprising sequences whose quantity or degree of representation (e.g., copy number) or sequence identity is known. A "reference nucleic acid sample" may be derived independently from a "test nucleic acid sample," i.e., the samples can be obtained from different organisms or different cell populations of the sample organism. However, in certain embodiments, a reference nucleic acid is present in a "test nucleic acid sample" which comprises one or more sequences whose quantity or identity or degree of representation in the sample is unknown while containing one or more sequences (the reference sequences) whose quantity or identity or degree of representation in the sample is known. The reference nucleic acid may be naturally present in a sample (e.g., present in the cell from which the sample was obtained) or may be added to or spiked in the sample.

A "negative control" probe or feature refers to a probe or feature that is designed not to bind with any of the sequences in the sample that is applied to the array on which the negative control probe or feature resides.

A "CGH array" or "aCGH array" refers to an array that can be used to compare DNA samples for relative differences in copy number. In general, an aCGH array can be used in any assay in which it is desirable to scan a genome with a sample of nucleic acids. For example, an aCGH array can be used in location analysis as described in U.S. Pat. No. 6,410,243, the entirety of which is incorporated herein. In certain aspects, a CGH array provides probes for screening or scanning a genome of an organism and comprises probes from a plurality of regions of the genome. In one aspect, the array comprises probe sequences for scanning an entire chromosome arm, wherein probes targets are separated by at least about 500 bp, at least about 1 kb, at least about 5 kb, at least about 10 kb, at least about 25 kb, at least about 50 kb, at least about 100 kb, at least about 250 kb, at least about 500 kb and at least about 1 Mb. In another aspect, the array comprises probes sequences for scanning an entire chromosome, a set of chromosomes, or the complete complement of chromosomes forming the organism's genome. By "resolution" is meant the spacing on the genome between sequences found in the probes on the array. In some embodiments (e.g., using a large number of probes of high complexity) all sequences in the genome can be present in the array. The spacing between different locations of the genome that are represented in the probes may also vary, and may be uniform, such that the spacing is substantially the same between sampled regions, or non-uniform, as desired. An assay performed at low resolution on one array, e.g., comprising probe targets separated by larger distances, may be repeated at higher resolution on another array, e.g., comprising probe targets separated by smaller distances.

In certain aspects, in constructing the arrays, both coding and non-coding genomic regions are included as probes, whereby "coding region" refers to a region comprising one or more exons that is transcribed into an mRNA product and from there translated into a protein product, while by non-coding region is meant any sequences outside of the exon regions, where such regions may include regulatory sequences, e.g., promoters, enhancers, untranslated but transcribed regions, introns, origins of replication, telomeres, etc. In certain embodiments, one can have at least some of the probes directed to non-coding regions and others directed to coding regions. In certain embodiments, one can have all of the probes directed to non-coding sequences. In certain embodiments, one can have all of the probes directed to coding sequences. In certain other aspects, individual probes comprise sequences that do not normally occur together, e.g., to detect gene rearrangements, for example.

In some embodiments, at least 5% of the polynucleotide probes on the solid support hybridize to regulatory regions of a nucleotide sample of interest while other embodiments may have at least 30% of the polynucleotide probes on the solid support hybridize to exonic regions of a nucleotide sample of interest. In yet other embodiments, at least 50% of the polynucleotide probes on the solid support hybridize to intergenic (e.g., non-coding) regions of a nucleotide sample of interest. In certain aspects, probes on the array represent random selection of genomic sequences (e.g., both coding and non-coding). However, in other aspects, particular regions of the genome are selected for representation on the array, e.g., such as CpG islands, genes belonging to particular pathways of interest or whose expression and/or copy number are associated with particular physiological responses of interest (e.g., disease, such a cancer, drug resistance, toxological responses and the like). In certain aspects, where particular genes are identified as being of interest, intergenic regions proximal to those genes are included on the array along with, optionally, all or portions of the coding sequence corresponding to the genes. In one aspect, at least about 100 bp, 500 bp, 1,000 bp, 5,000 bp, 10,000 kb or even 100,000 kb of genomic DNA upstream of a transcriptional start site is represented on the array in discrete or overlapping sequence probes. In certain aspects, at least one probe sequence comprises a motif sequence to which a protein of interest (e.g., such as a transcription factor) is known or suspected to bind.

In certain aspects, repetitive sequences are excluded as probes on the arrays. However, in another aspect, repetitive sequences are included.

The choice of nucleic acids to use as probes may be influenced by prior knowledge of the association of a particular chromosome or chromosomal region with certain disease conditions. International Application WO 93/18186 provides a list of exemplary chromosomal abnormalities and associated diseases, which are described in the scientific literature. Alternatively, whole genome screening to identify new regions subject to frequent changes in copy number can be performed using the methods discussed further below.

In some embodiments, previously identified regions from a particular chromosomal region of interest are used as probes. In certain embodiments, the array can include probes which "tile" a particular region (e.g., which have been identified in a previous assay or from a genetic analysis of linkage), by which is meant that the probes correspond to a region of interest as well as genomic sequences found at defined intervals on either side, i.e., 5' and 3' of, the region of interest, where the intervals may or may not be uniform, and may be tailored with respect to the particular region of interest and the assay objective. In other words, the tiling density may be tailored based on the particular region of interest and the assay objective. Such "tiled" arrays and assays employing the same are useful in a number of applications, including applications where one identifies a region of interest at a first resolution, and then uses tiled array tailored to the initially identified region to further assay the region at a higher resolution, e.g., in an iterative protocol.

In certain aspects, the array includes probes to sequences associated with diseases associated with chromosomal imbalances for prenatal testing. For example, in one aspect, the array comprises probes complementary to all or a portion of chromosome 21 (e.g., Down's syndrome), all or a portion of the X chromosome (e.g., to detect an X chromosome deficiency as in Turner's Syndrome) and/or all or a portion of the Y chromosome Klinefelter Syndrome (to detect duplication of an X chromosome and the presence of a Y chromosome), all or a portion of chromosome 7 (e.g., to detect William's Syndrome), all or a portion of chromosome 8 (e.g., to detect Langer-Giedon Syndrome), all or a portion of chromosome 15 (e.g., to detect Prader-Willi or Angelman's Syndrome, all or a portion of chromosome 22 (e.g., to detect Di George's syndrome).

Other "themed" arrays may be fabricated, for example, arrays to identify duplications or deletions which are associated with specific types of cancer (e.g., breast cancer, prostate cancer and the like). The selection of such arrays may be based on patient information such as familial inheritance of particular genetic abnormalities. In certain aspects, an array for scanning an entire genome is first contacted with a sample and then a higher-resolution array is selected based on the results of such scanning.

Themed arrays also can be fabricated for use in gene expression assays, for example, to detect expression of genes involved in selected pathways of interest, or genes associated with particular diseases of interest.

In one embodiment, a plurality of probes on the array are selected to have a duplex $T_m$ within a predetermined range. For example, in one aspect, at least about 50% of the probes have a duplex $T_m$ within a temperature range of about 75° C. to about 85° C. In one embodiment, at least 80% of said polynucleotide probes have a duplex $T_m$ within a temperature range of about 75° C. to about 85° C., within a range of about 77° C. to about 83° C., within a range of from about 78° C. to about 82° C. or within a range from about 79° C. to about 82° C. In one aspect, at least about 50% of probes on an array have range of $T_m$'s of less than about 4° C., less then about 3° C., or even less than about 2° C., e.g., less than about 1.5° C., less than about 1.0° C. or about 0.5° C.

The probes on the microarray, in certain embodiments have a nucleotide length in the range of at least 30 nucleotides to 200 nucleotides, or in the range of at least about 30 to about 150 nucleotides. In other embodiments, at least about 50% of the polynucleotide probes on the solid support have the same nucleotide length, and that length may be about 60 nucleotides.

In certain aspects, longer polynucleotides may be used as probes. In addition to the oligonucleotide probes described above, cDNAs, or inserts from phage BACs (bacterial artificial chromosomes) or plasmid clones, can be arrayed. Probes may therefore also range from about 201-5000 bases in length, from about 5001-50,000 bases in length, or from about 50,001-200,000 bases in length, depending on the platform used. If other polynucleotide features are present on a subject array, they may be interspersed with, or in a separately-hybridizable part of the array from the subject oligonucleotides.

In still other aspects, probes on the array comprise at least coding sequences.

In one aspect, probes represent sequences from an organism such as *Drosophila melanogaster, Caenorhabditis elegans*, yeast, zebrafish, a mouse, a rat, a domestic animal, a companion animal, a primate, a human, etc. In certain aspects, probes representing sequences from different organisms are provided on a single substrate, e.g., on a plurality of different arrays.

A "CGH assay" using an aCGH array can be generally performed as follows. In one embodiment, a population of nucleic acids contacted with an aCGH array comprises at least two sets of nucleic acid populations, which can be derived from different sample sources. For example, in one aspect, a target population contacted with the array comprises a set of target molecules from a reference sample and from a test sample. In one aspect, the reference sample is from an organism having a known genotype and/or phenotype, while the test sample has an unknown genotype and/or phenotype or a genotype and/or phenotype that is known and is different from that of the reference sample. For example, in one aspect, the reference sample is from a healthy patient while the test sample is from a patient suspected of having cancer or known to have cancer.

In one embodiment, a target population being contacted to an array in a given assay comprises at least two sets of target populations that are differentially labeled (e.g., by spectrally distinguishable labels). In one aspect, control target molecules in a target population are also provided as two sets, e.g., a first set labeled with a first label and a second set labeled with a second label corresponding to first and second labels being used to label reference and test target molecules, respectively.

In one aspect, the control target molecules in a population are present at a level comparable to a haploid amount of a gene represented in the target population. In another aspect, the control target molecules are present at a level comparable to a diploid amount of a gene. In still another aspect, the control target molecules are present at a level that is different from a haploid or diploid amount of a gene represented in the target population. The relative proportions of complexes formed labeled with the first label vs. the second label can be used to evaluate relative copy numbers of targets found in the two samples.

In certain aspects, test and reference populations of nucleic acids may be applied separately to separate but identical arrays (e.g., having identical probe molecules) and the signals from each array can be compared to determine relative copy numbers of the nucleic acids in the test and reference populations.

Methods to fabricate arrays are described in detail in U.S. Pat. Nos. 6,242,266; 6,232,072; 6,180,351; 6,171,797 and 6,323,043. As already mentioned, these references are incorporated herein by reference. Other drop deposition methods can be used for fabrication, as previously described herein. Also, instead of drop deposition methods, photolithographic array fabrication methods may be used. Interfeature areas need not be present particularly when the arrays are made by photolithographic methods as described in those patents.

Following receipt by a user, an array will typically be exposed to a sample and then read. Reading of an array may be accomplished by illuminating the array and reading the location and intensity of resulting fluorescence at multiple regions on each feature of the array. For example, a scanner may be used for this purpose is the AGILENT MICROARRAY SCANNER manufactured by Agilent Technologies, Palo, Alto, Calif. or other similar scanner. Other suitable apparatus and methods are described in U.S. Pat. Nos. 6,518,556; 6,486,457; 6,406,849; 6,371,370; 6,355,921; 6,320,196; 6,251,685 and 6,222,664. Scanning typically produces a scanned image of the array which may be directly inputted to a feature extraction system for direct processing and/or saved in a computer storage device for subsequent processing. However, arrays may be read by any other methods or apparatus than the foregoing, other reading methods including other optical techniques or electrical techniques (where each feature is provided with an electrode to detect bonding at that feature in a manner disclosed in U.S. Pat. Nos. 6,251,685, 6,221,583 and elsewhere).

An array is "addressable" when it has multiple regions of different moieties, i.e., features (e.g., each made up of different oligonucleotide sequences) such that a region (i.e., a "feature" or "spot" of the array) at a particular predetermined location (i.e., an "address") on the array will detect a particular solution phase nucleic acid sequence. Array features are typically, but need not be, separated by intervening spaces.

Figure 2:
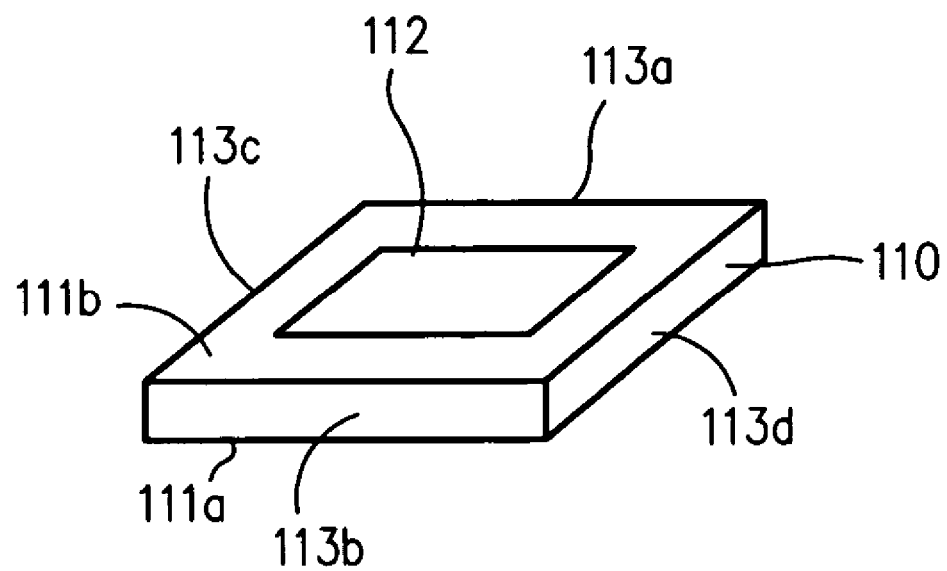
FIG. 2 illustrates an array.
Figure 3:
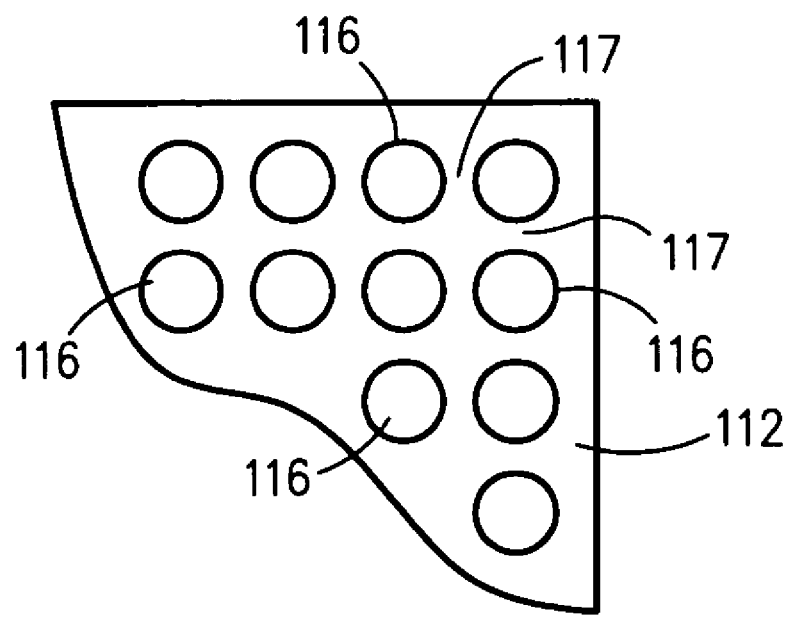
FIG. 3 illustrate a portion of the array of FIG. 2 in greater detail to show features thereon.

An exemplary array is shown in FIGS. 2-3, where the array shown in this representative embodiment includes a contiguous planar substrate 110 carrying an array 112 disposed on a surface 111b of substrate 110. It will be appreciated though, that more than one array (any of which are the same or different) may be present on surface 111b, with or without spacing between such arrays. That is, any given substrate may carry one, two, four or more arrays disposed on a surface of the substrate and depending on the use of the array, any or all of the arrays may be the same or different from one another and each may contain multiple spots or features. The one or more arrays 112 usually cover only a portion of the surface 111b, with regions of the surface 111b adjacent the opposed sides 113c, 113d and leading end 113a and trailing end 113b of slide 110, not being covered by any array 112. An opposite surface 111a of the slide 110 typically does not carry any arrays 112. Each array 112 can be designed for testing against any type of sample, whether a trial sample, reference sample, a combination of them, or a known mixture of biopolymers such as polynucleotides. Substrate 110 may be of any shape, as mentioned above.

As mentioned above, array 112 contains multiple spots or features 116 of oligomers, e.g., in the form of polynucleotides, and specifically oligonucleotides. As mentioned above, all of the features 116 may be different, or some or all could be the same. The interfeature areas 117 could be of various sizes and configurations. Each feature carries a predetermined oligomer such as a predetermined polynucleotide (which includes the possibility of mixtures of polynucleotides). It will be understood that there may be a linker molecule (not shown) of any known types between the surface 111b and the first nucleotide.

Substrate 110 may carry on surface 111a, an identification code, e.g., in the form of bar code (not shown) or the like printed on a substrate in the form of a paper label attached by adhesive or any convenient means. The identification code may contain information relating to array 112, where such information may include, but is not limited to, an identification of array 112, i.e., layout information relating to the array (s), etc.

In the case of an array in the context of the present application, the "target" may be referenced as a moiety in a mobile phase (typically fluid), to be detected by "probes" which are bound to the substrate at the various regions.

A "scan region" refers to a contiguous (preferably, rectangular) area in which the array spots or features of interest, as defined above, are found or detected. Where fluorescent labels are employed, the scan region is that portion of the total area illuminated from which the resulting fluorescence is detected and recorded. Where other detection protocols are employed, the scan region is that portion of the total area queried from which resulting signal is detected and recorded. For the purposes of this disclosure and with respect to fluorescent detection embodiments, the scan region includes the entire area of the slide scanned in each pass of the lens, between the first feature of interest, and the last feature of interest, even if there exist intervening areas that lack features of interest.

An "array layout" refers to one or more characteristics of the features, such as feature positioning on the substrate, one or more feature dimensions, and an indication of a moiety at a given location. "Hybridizing" and "binding", with respect to nucleic acids, are used interchangeably.

A "design file" is typically provided by an array manufacturer and is a file that embodies all the information that the array designer from the array manufacturer considered to be pertinent to array interpretation. For example, Agilent Technologies supplies its array users with a design file written in the XML language that describes the geometry as well as the biological content of a particular array.

A "design pattern" is a description of relative placement of features, with annotation. A grid template or design pattern can be generated from parsing a design file and can be saved/stored on a computer storage device. A grid template has basic grid information from the design file that it was generated from, which information may include, for example, the number of rows in the array from which the grid template was generated, the number of columns in the array from which the grid template was generated, column spacings, subgrid row and column numbers, if applicable, spacings between subgrids, number of arrays/hybridizations on a slide, etc. An alternative way of creating a grid template is by using an interactive grid mode provided by the system, which also provides the ability to add further information, for example, such as subgrid relative spacings, rotation and skew information, etc.

A "property" of an array, as used herein refers to a characteristic of an array that may be measured through analysis and calculation based on signals received during reading (e.g., scanning or other method of obtaining signals from) the array, and which may be used as a measure of quality of the array. Properties include, but are not limited to, noise, signal-to noise, background signal, signal intensity, uniformity/non-uniformity, etc.

A "probe signal", "probe value" or "probe signal value" refers to the ratio of a signal obtained from the probe to the signal of a target hybridized thereto, i.e., the signal from a probe bound to a target.

When one item is indicated as being "remote" from another, this is referenced that the two items are not at the same physical location, e.g., the items are at least in different buildings, and may be at least one mile, ten miles, or at least one hundred miles apart.

"Communicating" information references transmitting the data representing that information as electrical signals over a suitable communication channel (for example, a private or public network).

"Forwarding" an item refers to any means of getting that item from one location to the next, whether by physically transporting that item or otherwise (where that is possible) and includes, at least in the case of data, physically transporting a medium carrying the data or communicating the data.

A "processor" references any hardware and/or software combination which will perform the functions required of it. For example, any processor herein may be a programmable digital microprocessor such as available in the form of a mainframe, server, or personal computer. Where the processor is programmable, suitable programming can be communicated from a remote location to the processor, or previously saved in a computer program product. For example, a magnetic or optical disk may carry the programming, and can be read by a suitable disk reader communicating with each processor at its corresponding station.

Reference to a singular item, includes the possibility that there are plural of the same items present.

"May" means optionally.

Methods recited herein may be carried out in any order of the recited events which is logically possible, as well as the recited order of events.

All patents and other references cited in this application, are incorporated into this application by reference except insofar as they may conflict with those of the present application (in which case the present application prevails).

Methods, Systems and Computer Readable Media

The present disclosure provides methods, systems and computer readable media for detrending signal data extracted from an array, as well as design techniques that allow improved detrending and are useful for validating the results of detrending. Gradients (trends) in signal data, regardless of the effect or effects attributable to the gradient, may be detrended as long as the effects on the signals are proportional to the signals affected. Array designs provided allow trends (gradients resultant from processing and feature extracting an array) to be easily visualized and identified. Trends that such designs are adapted to facilitate the visualization of include, but are not limited to, multiplicative trends, hyb domes and spatial gradients due to ozone degradation.

Figure 4:
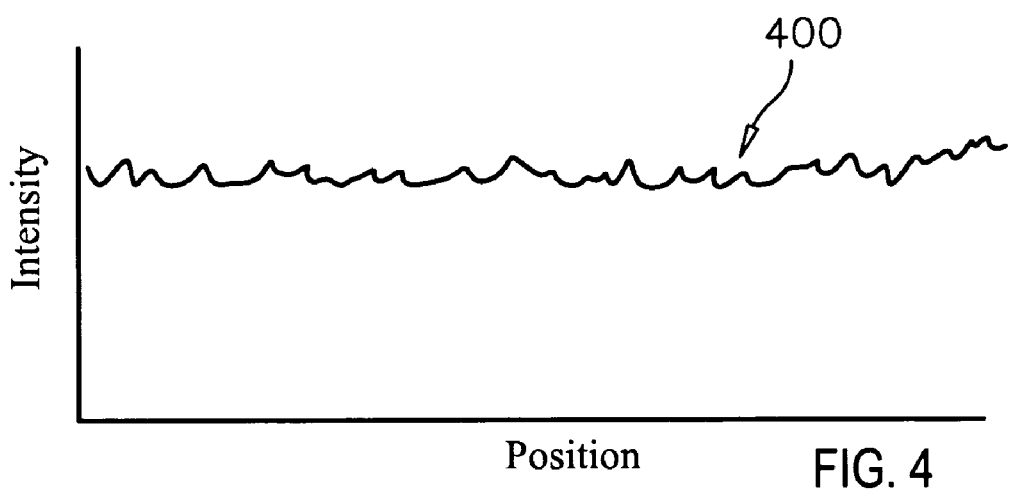
FIG. 4 is a schematic illustration of an idealized plot of probe signal values (intensity), by pixel (y-axis) plotted against positions (x-axis) of the pixels on an array.

FIG. 4 is a schematic illustration of an idealized plot 400 of probe signal values (intensity), by pixel (y-axis) plotted against positions (x-axis) of the pixels on an array where the array has been scanned and positions are plotted by column or by row, sequentially. The plot is idealized in the sense that essentially no gradients are present, which is reflected by the fact that the slope of the overall plot is effectively zero. The actual signal variation among pixels and probe signal values is a high frequency occurrence and is indicated by the small peaks and valleys of the plot 400 shown in FIG. 4. A smoothing function can be applied to the plot to eliminate the high frequency peaks and valleys, which, in this case, would result in a horizontal line.

Figure 5A:
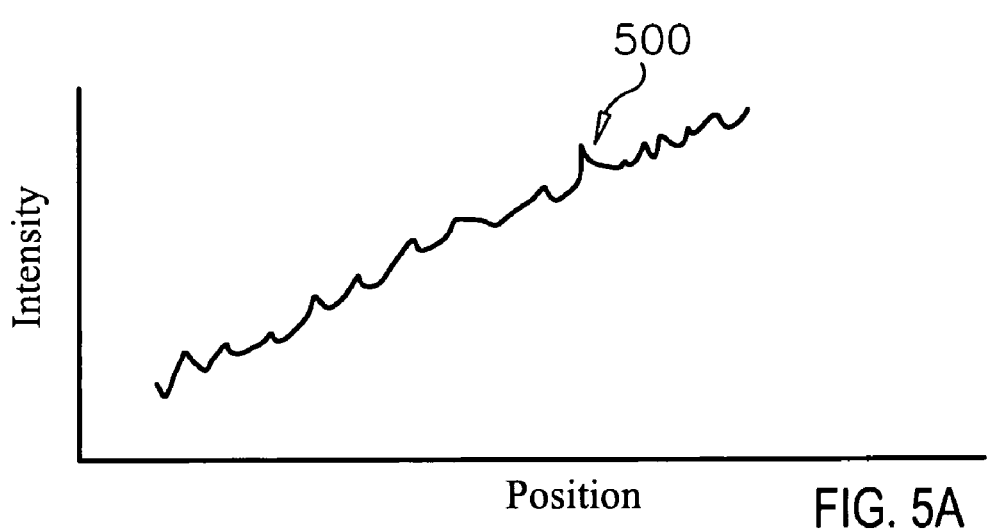
FIG. 5A is a schematic illustration of a plot of probe signal values that clearly exhibit a trend.
Figure 5B:
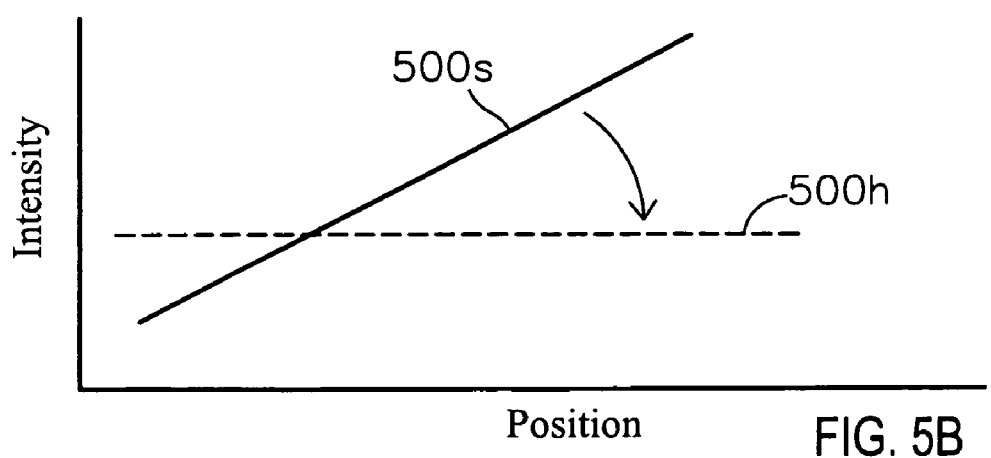
FIG. 5B illustrates the plot of FIG. 5A after smoothing has been accomplished.

FIG. 5A is a schematic illustration of a plot 500 that clearly exhibits a trend, as it can be noted that the values further to the right along the x-axis have significantly higher intensities (y-axis values) then those toward the left end of the x-axis. This could be representative of a multiplicative trend, for example. A multiplicative trend is formed when the signal values are multiplied relative to the amount of the true signal level, so that noise is somewhat proportional to the signal level of the feature. The process-induced gradient of the array represented by the plot 500 is characterized by the slope of the overall plot 500 which can be more readily quantified by smoothing the plot, using a smoothing algorithm selected from any number of well-known smoothing algorithms for such purposes, to remove the high frequency peaks and valleys that are representative of the probe signal values. FIG. 5B illustrates the plot 500s after smoothing has been accomplished. To remove the gradient, it is desirable that the resultant surface of values extracted from the array provide a flat plot, i.e., slope of zero. Accordingly, the plot 500s is analyzed to determine the slope thereof of the two-dimensional surface of the image, and the data values are adjusted accordingly to adjust the plot to a horizontal one 500h, such as by dividing the intensity values by the slope value in the case where the intensity values along the y-axis are log signal values, for example.

The signal plot can be characterized by a model that includes both additive and multiplicative noise, wherein the multiplicative noise is responsible for trends that are observed, and where the value of a pixel signal is given by $\alpha(x,y)*I+B(x,y)$, Where $B(x,y)$ represents the additive noise as a function of the x and y locations of the pixel on the grid of the array from which the signal is read, and $\alpha(x,y)$ represents the multiplicative noise as a function of the x and y locations of the pixel. Note that since $\alpha(x,y)$ is multiplied times the intensity I, it has a multiplicative effect on the surface gradient, relative to the intensity of the signal of each pixel.

The additive noise may be removed first, prior to processing to correct for the gradient caused by the multiplicative noise. The additive noise is not addressed by the presently disclosed techniques, but may be processed prior to the currently disclosed treatments for multiplicative trends. Thus, for the current approaches, it is assumed that any surface formed by additive noise is substantially flat, or the signals have been processed to adjust the additive noise so that that the additive noise forms a substantially flat surface. The additive noise factor is not dependent upon the signal level (signal received from scanning the probe).

For an entire array, the pixel intensities of the features may then be inputted and a surface fit may be calculated over the entire array, to output an approximated surface to thereby identify the gradients due to multiplicative factors in three dimensions. One example of an algorithm that may be used for approximating the surface fitting the pixel intensities over the array is a two dimensional polynomial surface fitting method, such as known in the art. Another example of an algorithm that may be used for approximating the surface fitting is a locally-weighted, least-squares regression method. One particular algorithm employing locally-weighted, least squares regression, is referred to as "Loess". The Loess method code implemented in the present disclosure can be obtained from the website netlib.org/a/Loess. A written description of the Loess method can be obtained from the website itl.nist.gov/div898/handbook/pmd/sectionl/pmdl44.htm, (Cleveland, W.S. (1979) "Robust Locally Weighted Regression and Smoothing Scatterplots," Journal of the American Statistical Association, Vol. 74, pp. 829-836, and Cleveland, W.S., and Deylin, S.J. (1988) "Locally Weighted Regression: An Approach to Regression Analysis by Local Fitting," Journal of the American Statistical Association, Vol. 83, pp. 596-610.) Other surface fitting algorithms may be substituted, as would be readily apparent to one of ordinary skill in the art. For example, polynomial surface fits using a polynomial of order other than second order may be used (e.g., first order, third order, fourth order, etc.).

Prior to calculating the surface fit of the signal intensities, but after removing additive noise, the signal intensity data may be further pre-processed according to various optional pre-processing steps. One such pre-processing step is to remove signal intensities of features, from the signal intensity data population, that have the lowest signals of the population. Thus a predetermined percentage of the lowest signal features may be removed, or those features having average signal intensities within a predetermined range of the calculated background noise level of the array may be excluded from further processing. Typically, signal values that are less than three standard deviations above the center of population (mean value) of the signals from the negative control probes (probes designed not to bind with sample and which, theoretically, should produce no signal intensity) on an array are excluded from processing for the surface fit used to determine and process multiplicative trending. Of course, thresholds other than the three standard deviation threshold just mentioned may be used alternatively to determine the signal level that is excluded.

Additionally, or alternatively, the log transform of each of the signal intensity values may be calculated and the log signal intensity values are then used to calculate the surface fit. By combining these processes, dim signals are removed from the population prior to the surface fit, so that noise has less effect on the calculation of the surface fit, and by log transforming the remaining signals the signal intensities are fit more equally into the surface fit, i.e., the size of the apparent gradient in log space is the same for all signal ranges and therefore the signal intensities affect the surface fit equally.

In order to remove the multiplicative gradient, the signals (pixel intensities) from the features of the array (after having been processed to remove additive noise, as noted) are divided by a factor calculated by the surface fit (obtained by Loess, polynomial, or other surface fitting algorithm as described above), where the surface fit is normalized to its mean (in this case, average). That is, the surface is calculated by the surface fitting algorithm from the signal intensities having had additive noise removed. Thus, the surface fit calculated by the surface fitting algorithm provides a value for every point (pixel value) on the array. The average fit value of all of the surface fit values for every feature location is then calculated. This average is then used to normalize the surface fit. If the surface fit is done in log space, then the average is subtracted from every surface fit value at every feature location in order to make the normalized surface fit. If the surface fit is performed in linear signal space, then every surface fit value is divided by the average value in order to make the normalized surface fit.

The signal intensity values are then de-trended using corresponding (by location) normalized surface value. For a surface fit calculated in linear signal space, the de-trending is performed by dividing the signal intensity value by the corresponding normalized surface fit value. For a surface fit calculated in log signal space, the normalized surface fit is first converted back to linear signal space, then the de-trending is performed by dividing the signal intensity value by the corresponding normalized surface fit value. In either case, because the surface fit has been normalized, the average signal intensity value does not change when de-trended, because the average normalized surface fit value is one.

Arrays may be designed specifically to allow improved detrending and better validation of the detrending. An "oversampled design" may be employed that contains a large number of replicates of each probe, wherein the replicates are randomly positioned across the array, i.e., located at random positions on the array. For example, more than ten replicates for each probe may be provided, typically twenty to fifty, more typically about twenty-five to thirty five. In one example, thirty replicates were provided on an array for each sequence/probe and this number of replicates was chosen to allow as many replicates as possible for each probe without concern for reduced signal from any probes due to target depletion. An oversampled array (i.e., array with oversampled design, as just described) allows trends to be more accurately measured, as the technical replicates of any one probe provide signals across the array which are all generally in the same range. Thus the differences between signals from different replicates of the same probe are more easily detected as each probe has greater representation due to the presence of the large number of replicates. However, in practice, it may not be practical in some instances to provide nearly as many replicates as described above. However the principles for detrending described herein still apply in the same manner for all arrays, even those for which no replicates are provided.

The use of the oversampled array design also may allow the surface fit to be performed (over the signal levels from each probe) more efficiently and more accurately. One difficulty that arises with typical surface fitting is that the signals resultant from feature extraction of the probes on the array can result in signal values that span three to four orders of magnitude, and it may not be clear as to whether the surface fit should consider the very high and very low signals as outliers or, rather, as extreme data points. When using an oversampled array, the signals from all replicates of any one probe may be normalized to an average signal level. After calculating average signal levels for each probe (from all replicates of that probe), the resultant average values are used to normalize the replicate probes so that the replicate intensities are centered around a predetermined intensity value, such as one, for example. These normalized values are then used an inputs for calculation of a surface fit. For example, these values may be inputs to the Loess algorithm running on a processor, wherein the processor then calculates and outputs the parameters of the surface fit.

Another alternative technique for surface fitting (and subsequent gradient processing) reduces the time for calculating the surface fit. In the approach described above, all data points (i.e., signal values from all features on the array) are inputted into Loess to calculate the surface fit. The time required to run Loess calculations is proportional to $N^2$ or $N \log N$, where N represents the number of data points (e.g., signal values) inputted to Loess to use in performing a surface fit calculation. By reducing the number of data points (signal values) inputted to Loess to calculate the surface fit, the processing time can be significantly reduced. The present approach does this without significant reduction in the accuracy of the surface fit by using all the data, but locally averaging signals from groups of nearest neighbors of probes (local area, as spatially located on the array). For example, a typical "local area" of nearest neighbors of data points that may be averaged may be on the order of 9 points (features), i.e., a square of 3×3 features, although the local area may be as small as 2×2 features or larger than 3×3 features, such as 4×4 features, 5×5 features or even larger. Of course there is an inverse relationship between the local area size and processing time, and also resolution decreases as local area size increases. Each local area averages out any effect of widely varying signal levels that may be present. The average signal values for each local area are then inputted into Loess, including for each location, the average signal of its nearest neighbors. The term "location" here represents the center of the local area. Thus, for example, when local areas of 3×3 features each are used, the "locations" inputted, i.e., the centers of these local areas amount to only one ninth of all loci on the array. In one example, local areas were defined by regions of three features by three features area and average values were inputted for every other location (feature) from which a signal was received in both x and y directions along the array, thereby reducing the number of features inputted by a factor of four. This reduced the LOESS processing time for calculating a surface fit of 44,000 features to less than one minute, whereas when signals from all features were inputted, the processing time was about fifteen minutes. The resultant fit, using the averaging technique described, was determined to be of sufficient accuracy, relative to the fit calculated when signals from all features were inputted. In contrast, when simply reducing the number of data points (signals) inputted to LOESS, without local averaging (i.e., simply using the signal values of the probes obtained from the locations used for inputting), the surface fit produced was significantly inferior in accuracy compared to the surface fit calculated using all signal values.

Variations in signal value (which may be referred to as noise) can be decomposed into an additive term plus a multiplicative term. The additive term is not dependent upon the signal level (signal received from scanning the probe), while the multiplicative term is proportional to the intensity of the signal level, with this noise factor (multiplicative term) increasing as the signal level increases, (e.g., multiplicative factor (M) times the signal level). Therefore, in the very low signal range, such as with "dim" features, the noise is dominated by the additive term and noise is not proportional to the signal level in that range. As the signal level increases, the factor M times signal level becomes significantly greater then the additive term and thus controls in the definition of noise. Therefore, noise becomes proportional to the signal level in this range. Thus, when considering very dim features during surface fitting and multiplicative detrending, an additive trend resultant from additive noise in the signals may be overly represented and distort the multiplicative trend that is sought to be identified. Accordingly, the system provides a filter that excludes features that are too dim, e.g., features, which when processed by feature extraction, give signals, the variations in which are too small to distinguish from background noise. Typically, features having signal values that are less than three standard deviations above the center of population (mean value) of the signals from the negative control probes on the array are excluded from processing for the surface fit used to determine and process multiplicative trending. Of course, other thresholds other than the three standard deviation threshold just mentioned may be used alternatively to determine the signal level for excluding features having signal levels below the determined signal level.

Using the multiplicative detrending techniques discussed, testing has shown that both intra-and inter-array % CV (percentage of coefficient of variation) values have been reduced, compared to % CV values for the same arrays that were not processed for multiplicative detrending.

Figure 6A:
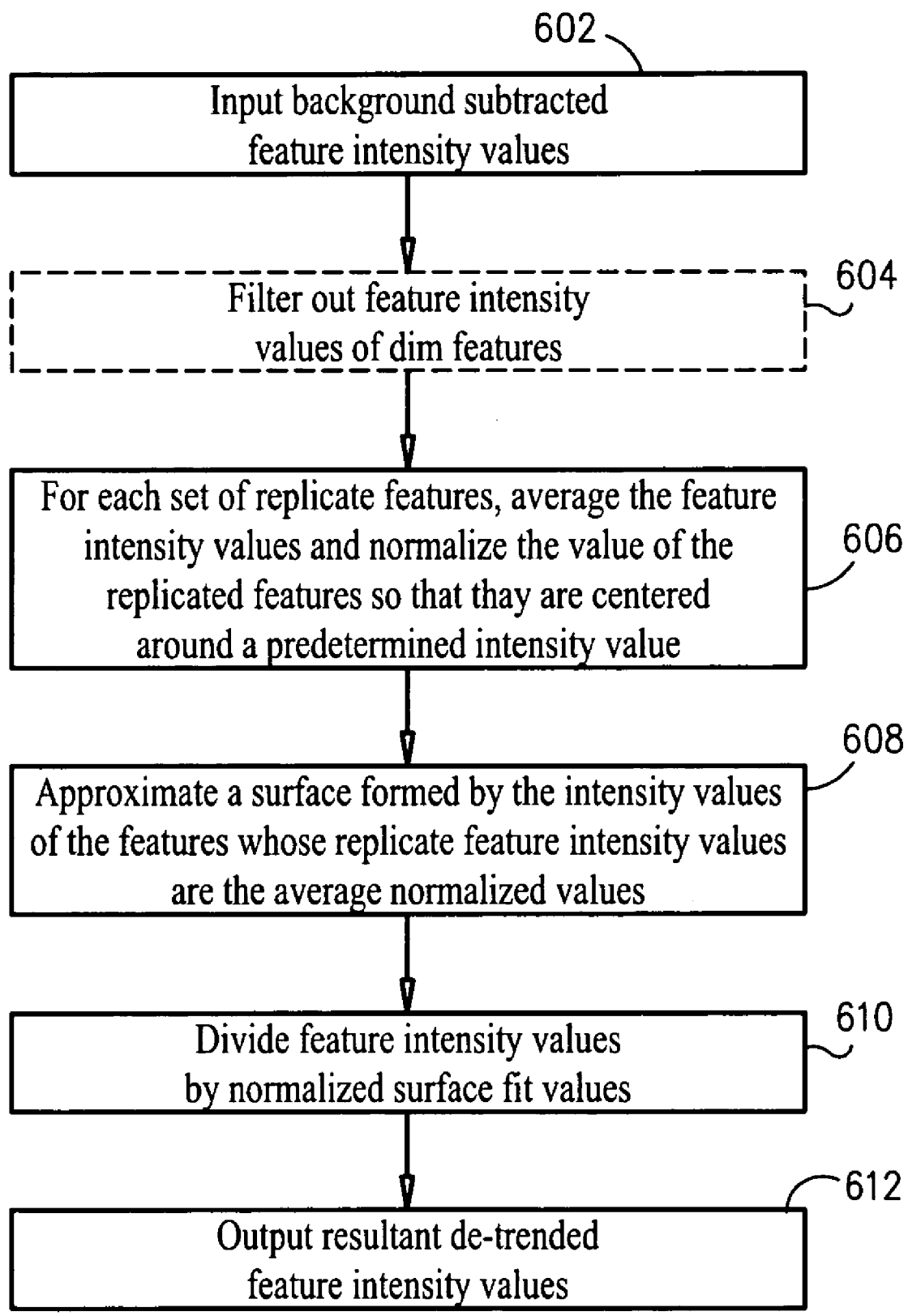
FIG. 6A shows events that may be carried out in processing feature intensity signals to detrend the signal intensity values, when using an oversampled array.

FIG. 6A shows events that may be carried out in processing feature intensity signals to detrend the signal intensity values, when using an oversampled array.

At event 602, signal intensity values of features which have already been processed to remove additive noise and thereby subtract background signals. Background subtraction (removal of additive noise) may be carried out, for example, by using Agilent Feature Extraction software. The background subtracted signals, having been processed to remove additive noise, are inputted to the present system. Such values may be obtained from a stored file resulting from feature extraction of the features on an array for example, as stored in primary storage 704 or 706, mass storage 708, or on another storage device, such as a CD or DVD ROM 714, or other storage device as known in the art. Alternatively, these values may be directly inputted from the output of a feature extraction process. Further initial filtering may be performed, in addition to background subtraction, prior to event 602, including, but not limited to, filtering to remove signals from: non-uniform features, saturated features, signals from control features such as negative controls (designed not to bind with sample) and/or positive controls, such as spike-ins, etc., and/or signals from features calculated to be statistical outliers and that therefore are not used in surface fitting the data.

Further, at event 604, the system may optionally filter out signal intensity values of dim features, such as features whose intensity values are too small to distinguish from background noise. For example, dim features may be defined as those having signal intensities less than or equal to a predetermined threshold intensity value. One example of a predetermined threshold signal intensity value is a multiplier times a standard deviation of population distribution of the signals from the negative control probes on the array. Such predetermined threshold signal intensity value may be user settable, and may be input by a user through a user interface 710, for example.

At event 606, the system calculates an average signal intensity value for a set of replicate values, and performs such calculation for each set of replicate features. For each set of replicate features, the values of the replicate features are then normalized so that they are centered around a predetermined intensity value, as was described previously. For example, each set of replicates may be normalized around the value of one.

Using the averaged normalized intensity values of the features that are members of a replicate set, these intensity values, encoded with their respective locations on the array, are used to calculate an approximation of a surface over all locations on the array at event 608, wherein the surface is a best fit through the intensity values as plotted on a z-axis of a three dimensional plot wherein the x and y axes plot the locations of the features.

At event 610, the surface fit values, i.e., the values on the surface fit at locations corresponding to the location of the features from which feature intensity values were inputted at event 602, are averaged, to calculate an average (e.g., mean) surface fit value. The surface fit values are then normalized by dividing each surface fit value by the average surface fit value. The background-subtracted signal intensity values from event 602 are then de-trended by dividing each background-subtracted signal value by the normalized surface fit value that corresponds to the location of the feature from which the background-subtracted signal value originated.

At event 612, the system outputs signal intensity values having been corrected for multiplicative trending noise, to remove such noise. Outputs may be in the form of numeric results visualized on a monitor of a user interface 710, and/or may be printed out on paper or written to other recordable media. Additionally, or alternatively, output results at event 612 may be transmitted to another location, such as via a network connection 712, for example.

Figure 6B:
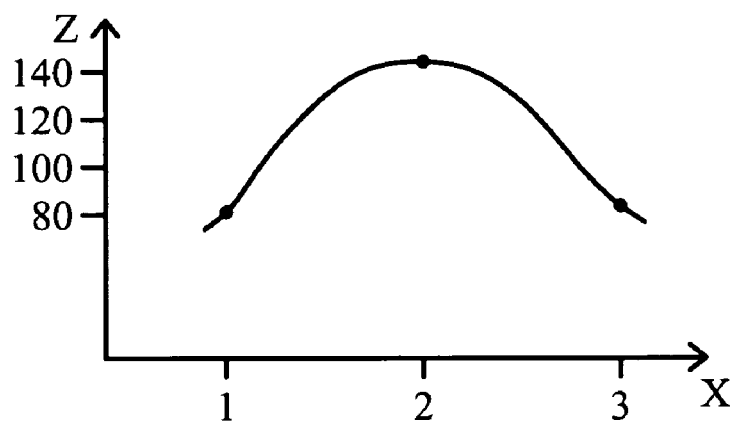
FIGS. 6B-6D are simplified plots illustrating de-trending a surface gradient from signal intensity data.
Figure 6C:
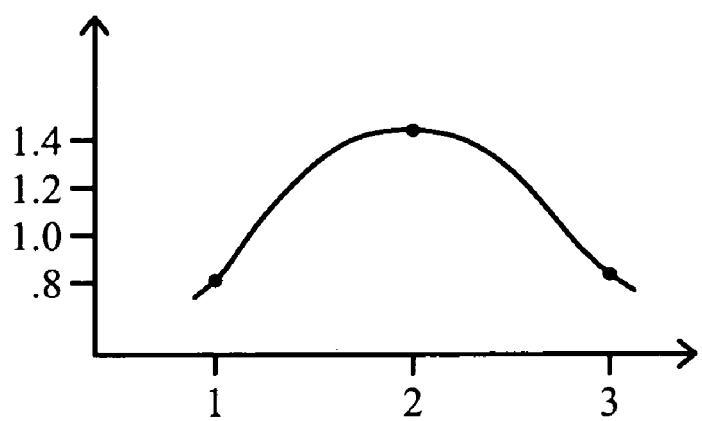

FIG. 6B illustrates an extremely simplified example of signal intensity data points exhibiting a trending pattern, in this case a hybridization dome. For purposes of simplifying the explanation, signal intensity features in only one dimension are shown (X-axis) versus signal intensity (Z-axis) and signal intensities from only three features are represented. In actual practice there will typically be hundreds, thousands or tens of thousands of features along the X-axis as well as along the Y-axis (which is not even shown in this simple example), so that a two dimensional surface is fitted over the signal intensity values. In this case, features 1 and 3 each have a signal intensity of about 80 and feature 2 has a signal intensity of about 140. If a surface fit is performed and the surface fit values are divided by the average surface fit value then the resulting normalized surface fit values still exhibit the trending pattern as illustrated in FIG. 6C (i.e., feature 1=80/100=0.8, feature 2=140/100=1.4, feature 3=80/100=0.8). Thus, the shape of the hybridization dome is still present in the surface fit that has been normalized from this processing in FIG. 6C. (but the average surface fit value is now one).

Figure 6D:
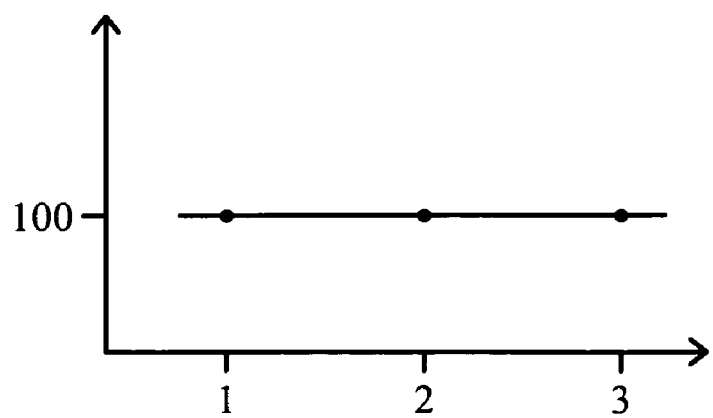

By normalizing the surface fit values (i.e., divide each surface fit value by the average surface fit value of 100) and then processing the signal intensity values to divide them by the correspondingly located, normalized surface fit values as described, the trend is removed from the resulting values as illustrated in FIG. 6D (i.e., feature 1=80/0.8=100, feature 2=140/1.4=100, feature 3=80/0.8=100). Thus, the trend of the feature signal data has been removed, leaving a flat surface (or line, in this example). Also, because the surface fit was normalized to have an average of one, the de-trending has not changed the average of the linear feature signals (i.e., their average is 100 before and after de-trending).

Figure 6E:
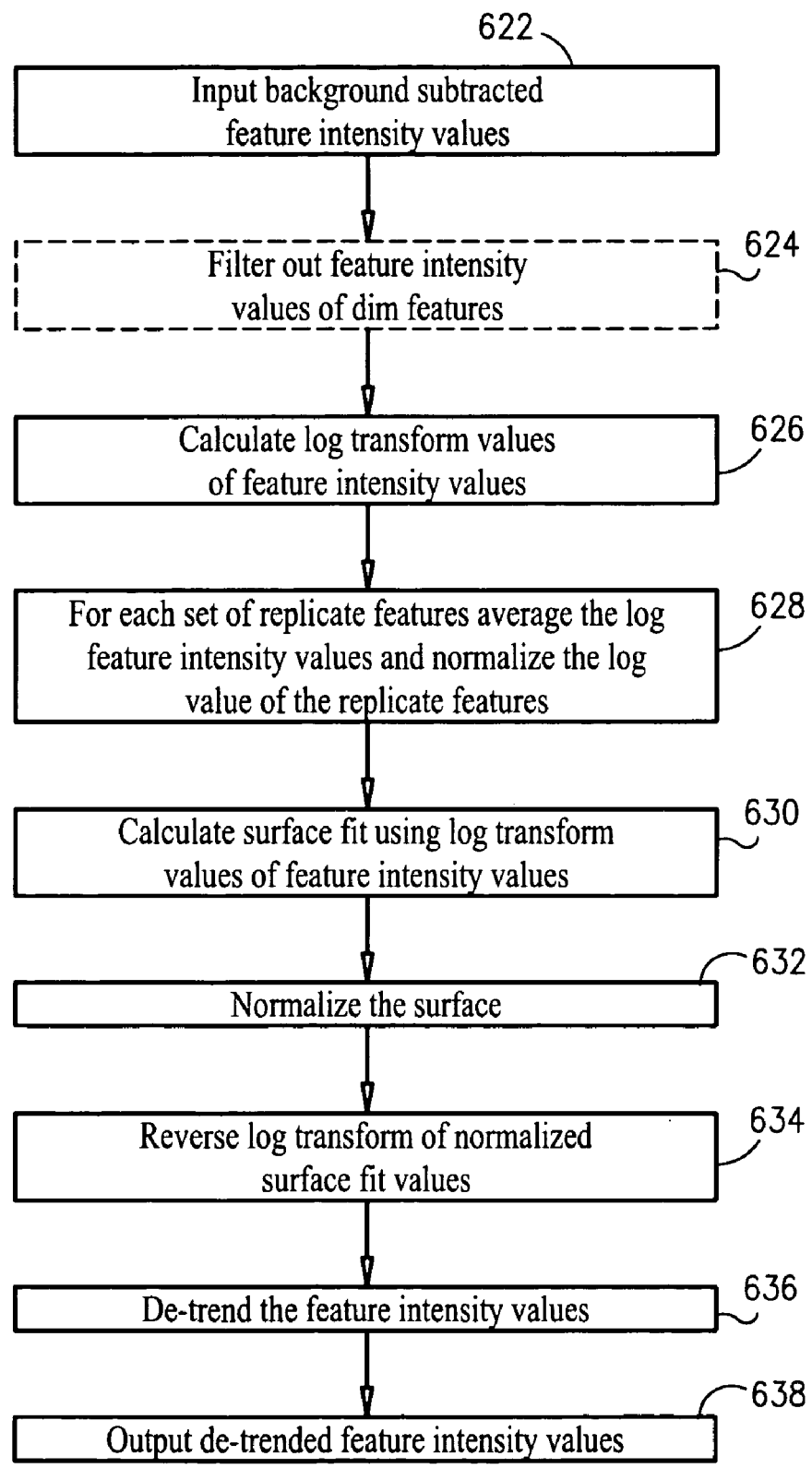
FIG. 6E shows events that may be carried out in processing feature intensity signals to de-trend the signal intensity values, in an alternative manner to that described with regard to FIG. 6A.

FIG. 6E shows events that may be carried out in processing feature intensity signals to de-trend the signal intensity values, in an alternative manner to that described above with regard to FIG. 6A.

At event 622, signal intensity values of features which have already been processed to remove additive noise and to subtract background signals. Background subtraction (additive noise removal) may be carried out as described with regard to FIG. 6A, for example, or by using other available packages for background subtraction. The background subtracted signals, having been processed to remove additive noise, are inputted to the present system. Such values may be obtained from a stored file resulting from feature extraction of the features on an array for example, as stored in primary storage 704 or 706 (FIG. 8), mass storage 708, or on another storage device, such as a CD or DVD ROM 714, or other storage device as known in the art. Alternatively, these values may be directly inputted from the output of a feature extraction process. Further initial filtering may be performed, in addition to background subtraction, prior to event 622, including, but not limited to, filtering to remove signals from: non-uniform features, saturated features, signals from control features such as negative controls (designed not to bind with sample) and/or positive controls, such as spike-ins, etc., and/or signals from features calculated to be statistical outliers and that therefore are not used in surface fitting the data.

Further, at event 624, the system may optionally filter out signal intensity values of dim features (such filtering may be user selectable), such as features whose intensity values are too small to distinguish from background noise. For example, dim features may be defined as those having signal intensities less than or equal to a predetermined threshold intensity value. One example of a predetermined threshold signal intensity value is a multiplier times a standard deviation above the center of population (mean value) of the signals from the negative control probes on the array. Such predetermined threshold signal intensity value may be user settable, and may be input by a user through a user interface 710, for example.

At event 626, the system calculates the log transform value of each signal (feature) intensity value that has not already been filtered out. At event 628, if the user has chosen to use groups of replicate features rather than all features that have not already been filtered out, and replicate features are present, an average log intensity value for each set of replicate feature intensity values is calculated and the log feature intensity values of the replicated features are normalized around a predetermined intensity value. In log space, the predetermined intensity value is zero. Alternatively, all features that have not already been filtered out are used to perform the surface fit.

At event 630 a surface fit of the intensity values of the features is calculated using the log transform values of the feature intensity values, where the feature intensity values used are either from all features which have not already been filtered out, or the average feature intensity values of replicate groups, where replicate groups are used instead of all features that have not already been filtered out, and where replicate feature intensity values are represented by the log transform of the averaged normalized values for the replicate sets. By log transforming the feature intensity signals, the signal intensity values (log values) are fit more equally into the surface fit, that is, the size of the apparent gradient of the surface in log space is the same for all signal ranges and therefore the signal intensity affect the surface fit equally.

At event 632, the calculated surface (surface fit) of the log feature intensity signals is normalized by subtracting the average surface fit value from each surface fit value that was calculated for the surface. These normalized surface fit values are then reverse log transformed at event 634.

The normalized surface values (no longer in log space) are then used to de-trend the feature intensity values at event 636 by dividing the feature intensity values by the normalized surface fit values at corresponding locations on the surface.

At event 638, the system outputs signal intensity values having been corrected for multiplicative trending noise, to remove such noise. Outputs may be in the form of numeric results visualized on a monitor of a user interface 710, and/or may be printed out on paper or written to other recordable media. Additionally, or alternatively, output results at event 612 may be transmitted to another location, such as via a network connection 712, for example.

Figure 7:
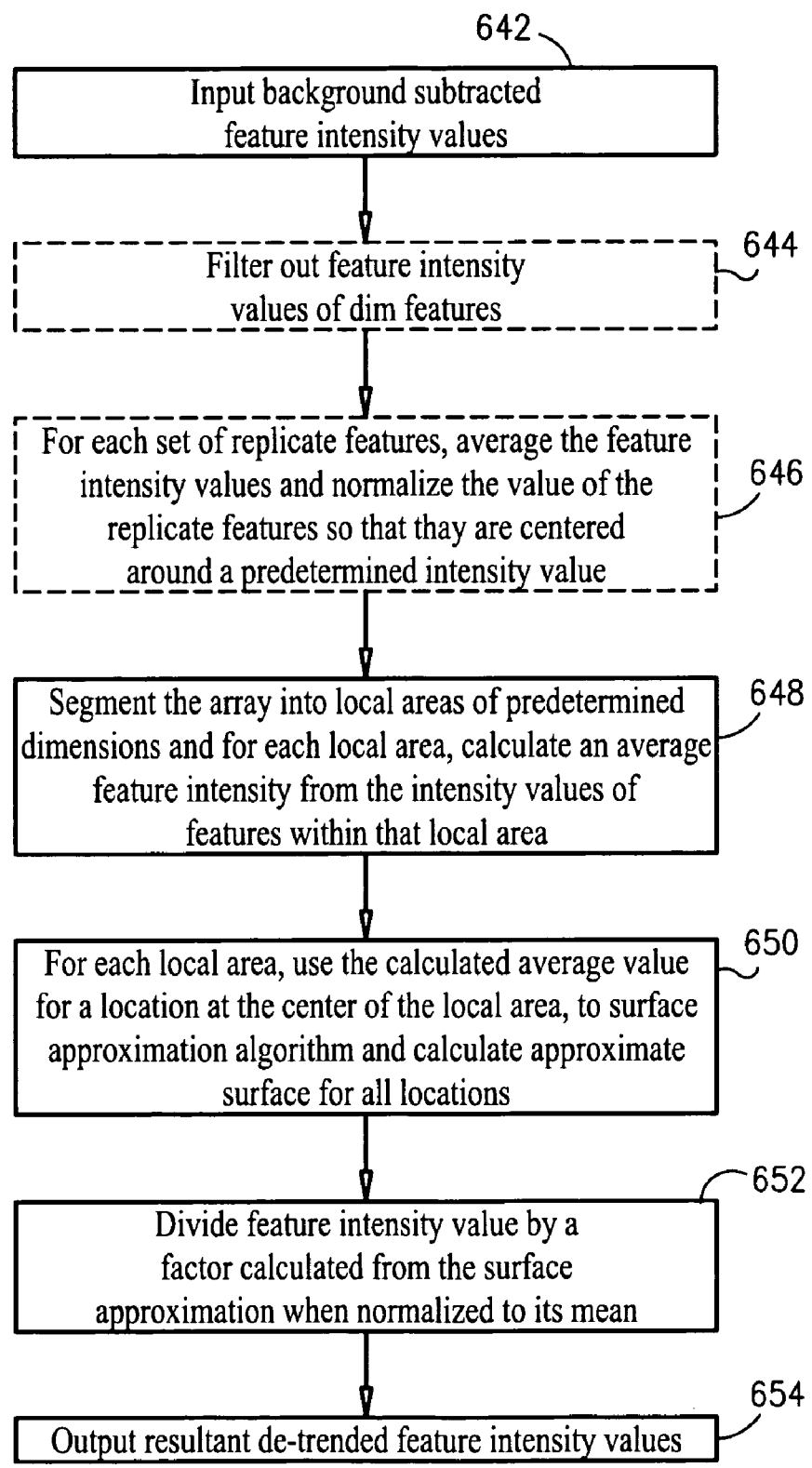
FIG. 7 shows events that may be carried out in processing feature intensity signals to detrend the signal intensity values thereof.

FIG. 7 shows events that may be carried out in processing feature intensity signals to detrend the signal intensity values thereof, including another aspect disclosed herein.

At event 642, signal intensity values of features which have already been processed for background subtraction are inputted to the present system. Such values may be obtained from a stored file resulting from feature extraction of the features on an array for example, as stored in primary storage 704 or 706, mass storage 708, or on another storage device, such as a CD or DVD ROM 714, or other storage device as known in the art. Alternatively, these values may be directly inputted from the output of a feature extraction process. Further initial filtering may be performed, in addition to background subtraction, prior to event 642, including, but not limited to, filtering to remove signals from: non-uniform features, saturated features, signals from control features such as negative controls (designed not to bind with sample) and/or positive controls, such as spike-ins, etc., and/or signals from features calculated to be statistical outliers and that therefore are not used in surface fitting the data.

Further, at event 644, the system may optionally filter out signal intensity values of dim features, such as features whose intensity values are too small to distinguish from background noise. For example, dim features may be defined as those having signal intensities less than or equal to a predetermined threshold intensity value One example of a predetermined threshold signal intensity value is a multiplier times a standard deviation above the center of population (mean value) of the signals from the negative control probes on the array. Such predetermined threshold signal intensity value may be user settable, and may be input by a user through a user interface 710, for example.

At event 646, if replicates of features exist on the array from which signal intensity values are being processed, the system may optionally calculate an average signal intensity value for each set of replicate features. For each set of replicate features, the values of the replicate features are then normalized so that they are centered around a predetermined intensity value, as was described previously.

At event 648, the system considers local areas of features, wherein the array on which the features exist is considered to be segmented into local areas of predetermined dimensions. The predetermined dimensions of the local areas may be automatically set by the system, or may be user selectable, such as through user interface 710, for example. For each local area, an average signal intensity is calculated from the feature intensities of the features that are included in that local area.

The average signal intensity from each local area is next used, at event 650, along with the corresponding locations of the centers of the local areas, to calculate a surface approximation across all locations on the array. The surface approximation is a best fit through the average intensity values used, as plotted on a z-axis of a three dimensional plot wherein the x and y axes plot the locations of the features. The surface fit generates a value for every feature on the array, not just the local average locations.

At event 652, the surface fit values are averaged, to calculate an average (e.g., mean) surface fit value. The surface fit values at all locations on the surface corresponding to locations of all of the features on the array are then normalized by dividing each surface fit value by the average surface fit value. The background-subtracted signal intensity values from event 642 are then de-trended by dividing each background-subtracted signal value by the normalized surface fit value that corresponds to the location of the feature from which the background-subtracted signal value originated.

At event 654, the system outputs signal intensity values of features having been corrected for multiplicative trending noise, to remove such noise. Outputs may be in the form of numeric results visualized on a monitor of a user interface 710, and/or may be printed out on paper or written to other recordable media. Additionally, or alternatively, output results at event 634 may be transmitted to another location, such as via a network connection 712, for example.

Figure 8:
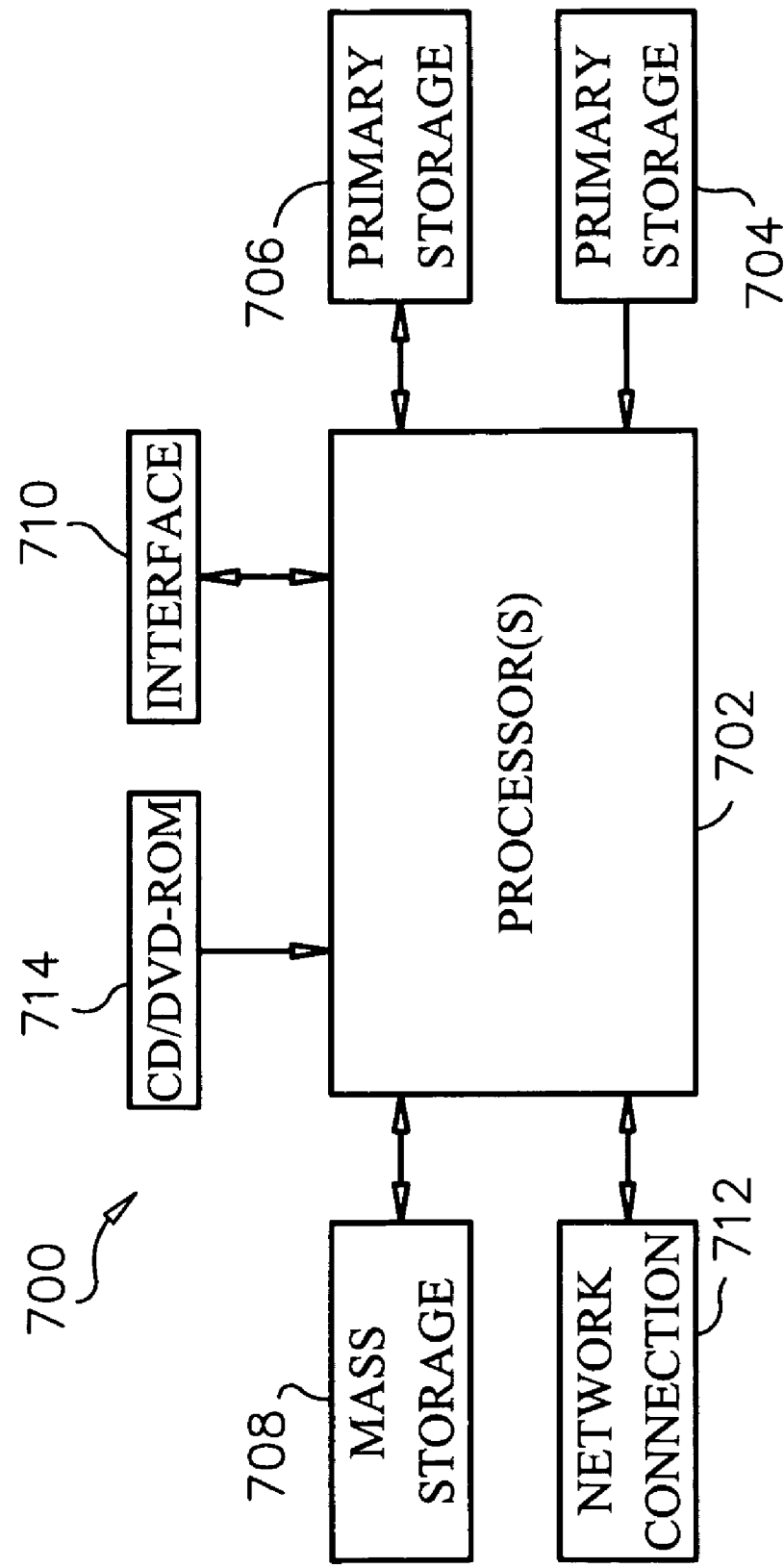
FIG. 8 is a schematic illustration of a typical computer system that may be used to perform processing described herein.

FIG. 8 is a schematic illustration of a typical computer system that may be used to perform procedures described above. The computer system 700 includes any number of processors 702 (also referred to as central processing units, or CPUs) that are coupled to storage devices including primary storage 706 (typically a random access memory, or RAM), primary storage 704 (typically a read only memory, or ROM). As is well known in the art, primary storage 704 acts to transfer data and instructions uni-directionally to the CPU and primary storage 706 is used typically to transfer data and instructions in a bi-directional manner Both of these primary storage devices may include any suitable computer-readable media such as those described above. A mass storage device 708 is also coupled bi-directionally to CPU 702 and provides additional data storage capacity and may include any of the computer-readable media described above. Mass storage device 708 may be used to store programs, data and the like and is typically a secondary storage medium such as a hard disk that is slower than primary storage. It will be appreciated that the information retained within the mass storage device 708, may, in appropriate cases, be incorporated in standard fashion as part of primary storage 706 as virtual memory. A specific mass storage device such as a CD-ROM or DVD-ROM 714 may also pass data uni-directionally to the CPU.

CPU 702 is also coupled to an interface 710 that includes one or more input/output devices such as video monitors, track balls, mice, keyboards, microphones, touch-sensitive displays, transducer card readers, magnetic or paper tape readers, tablets, styluses, voice or handwriting recognizers, or other well-known input devices such as, of course, other computers. Finally, CPU 702 optionally may be coupled to a computer or telecommunications network using a network connection as shown generally at 712. With such a network connection, it is contemplated that the CPU might receive information from the network, or might output information to the network in the course of performing the above-described method steps. The above-described devices and materials will be familiar to those of skill in the computer hardware and software arts.

The hardware elements described above may implement the instructions of multiple software modules for performing the operations of this disclosure. For example, instructions for calculating average signal values may be stored on mass storage device 708 or 714 and executed on CPU 708 in conjunction with primary memory 706.

In addition, embodiments of the present disclosure further relate to computer readable media or computer program products that include program instructions and/or data (including data structures) for performing various computer-implemented operations. The media and program instructions may be those specially designed and constructed for the purposes of the present disclosure, or they may be of the kind well known and available to those having skill in the computer software arts. Examples of computer-readable media include, but are not limited to, magnetic media such as hard disks, floppy disks, and magnetic tape; optical media such as CD-ROM, CDRW, DVD-ROM, or DVD-RW disks; magneto-optical media such as floptical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

EXAMPLES

The following examples are put forth so as to provide those of ordinary skill in the art with a complete at least one embodiment described herein, disclosure and description of how to make and use and are not intended to limit the scope of what the inventors regard as their invention nor are they intended to represent that the experiments below are all or the only experiments performed. Efforts have been made to ensure accuracy with respect to numbers used (e.g. amounts, percentages, etc.) but some experimental errors and deviations should be accounted for.

Example 1

An oversampled array was processed to determine whether the shape of the gradient of the signals, produced from feature extracting the features on the array, is dependent upon the intensity range of the signals. The array included 1410 different probes specific to 1410 different sequences and was provided with thirty replicates for each probe, randomly distributed over the array. The array was used for a two channel scanner, to extract both red and green signals from each probe. After feature extraction, the signals received for each channel were background subtracted and average signals were calculated for each probe, for each channel, wherein all thirty signal values were averaged in each case. The background subtraction determined a local value of the intensity of features with no intentionally bound dye-labeled target (i.e., negative control features). This local value was determined by calculating a surface fit over the signal intensity values of the negative control features. Thus a local value for each corresponding location of the non-control features is determined along the calculated surface. The values on the calculated surface corresponding to each non-negative control feature are then subtracted from the signal intensities of the features in the locations on the array that correspond to the locations of the values on the calculated surface to provide the background subtracted signal intensities of the non-control features. Agilent's Feature Extraction Software (Agilent Technologies, Inc., Palo Alto, Calif.) was used to perform the background subtraction. Saturated features, non-uniform features and dim features (i.e., those feature having intensity less than three standard deviations above the center of population of signals from negative control features) were also filtered out. For each channel, the average signal values were ranked and grouped into three bins, the bottom third of the ranked, averaged signals being assigned to one bin, the middle third of the ranked, averaged signals being assigned to a second bin, and the top third of the ranked, averaged signals being assigned to a third bin. Probe names were maintained in association with each average value for identification purposes. Accordingly, 470 average signals were contained in each bin.

Next the averaged background-subtracted signal data in each of the bins was fitted to a surface. The surface resulting from a two-dimensional polynomial surface fit was then normalized at every data point (feature signal value) to the average of the surface.

Figure 9A:
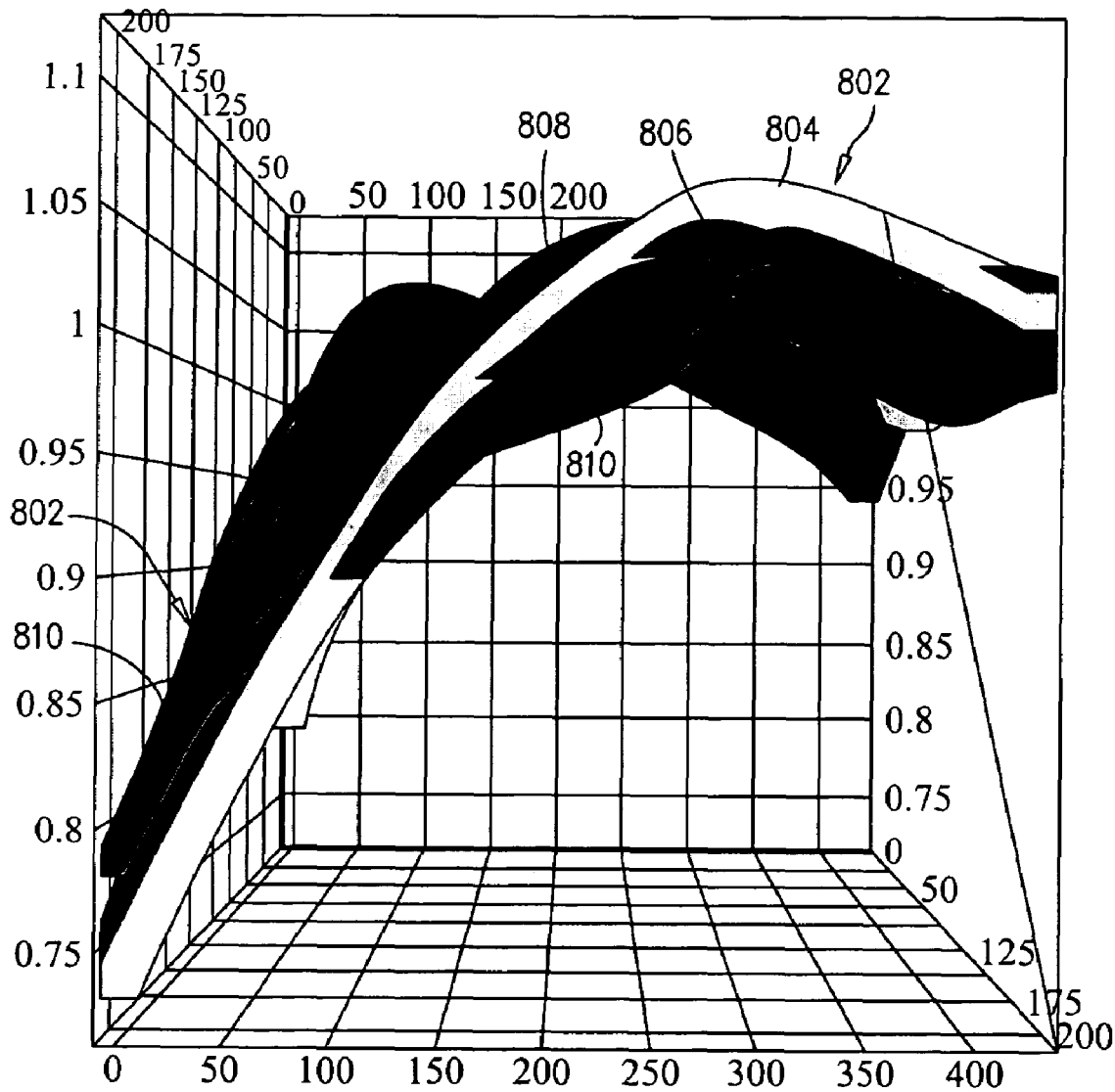
FIG. 9A is a scatter plot showing a surface fit to background subtracted signals from a green channel for all probes on an array.
Figure 9B:
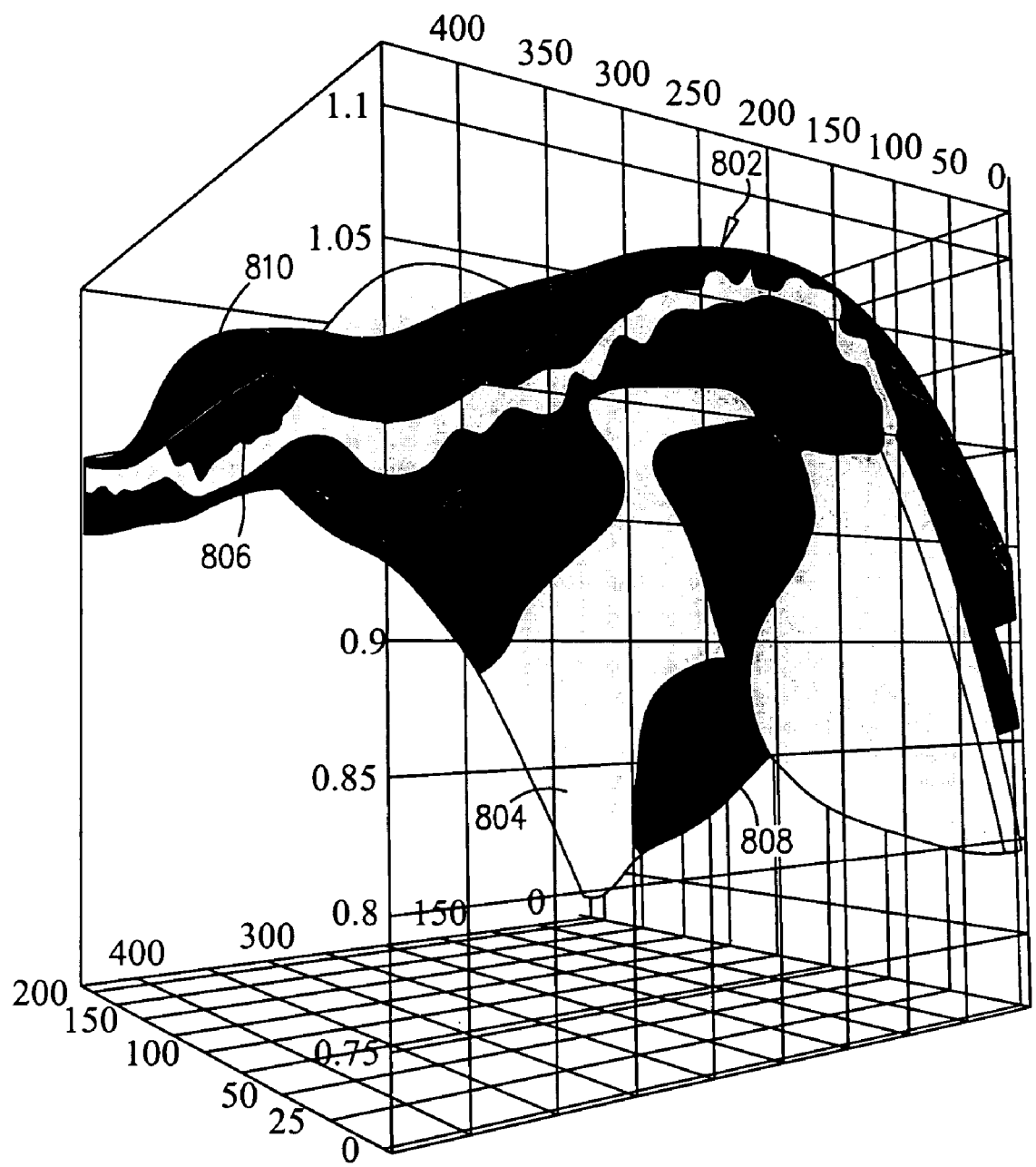
FIG. 9B is the plot of FIG. 9A having been rotated about axis 1 by 180 degrees.

FIG. 9A is a scatter plot 802 showing the surface fit to the background subtracted signals from the green channel for all probes on the array. The lightest color portion (grey-green) 804 is a plot of the surface fitted to the background-subtracted signals from the bin containing the highest signal intensity values, the red portions 806 plot the surface fitted to the background-subtracted signals from the bin containing the dimmest, or lowest signal intensity values, the maroon portions 808 plot the surface fitted to the background-subtracted signals from the bin containing the medium intensity signals, and the pink portions 810 plot the fit averaging of each sequence to the average value of the signal intensities of the replicates of that sequence. Signal values are plotted on axis 1 with respect to the x and y locations relative to the array on axes 2 and 3. FIG. 9B shows the same data which has been rotated by about one hundred eighty degrees about the vertical (intensity) axis.

Figure 10A:
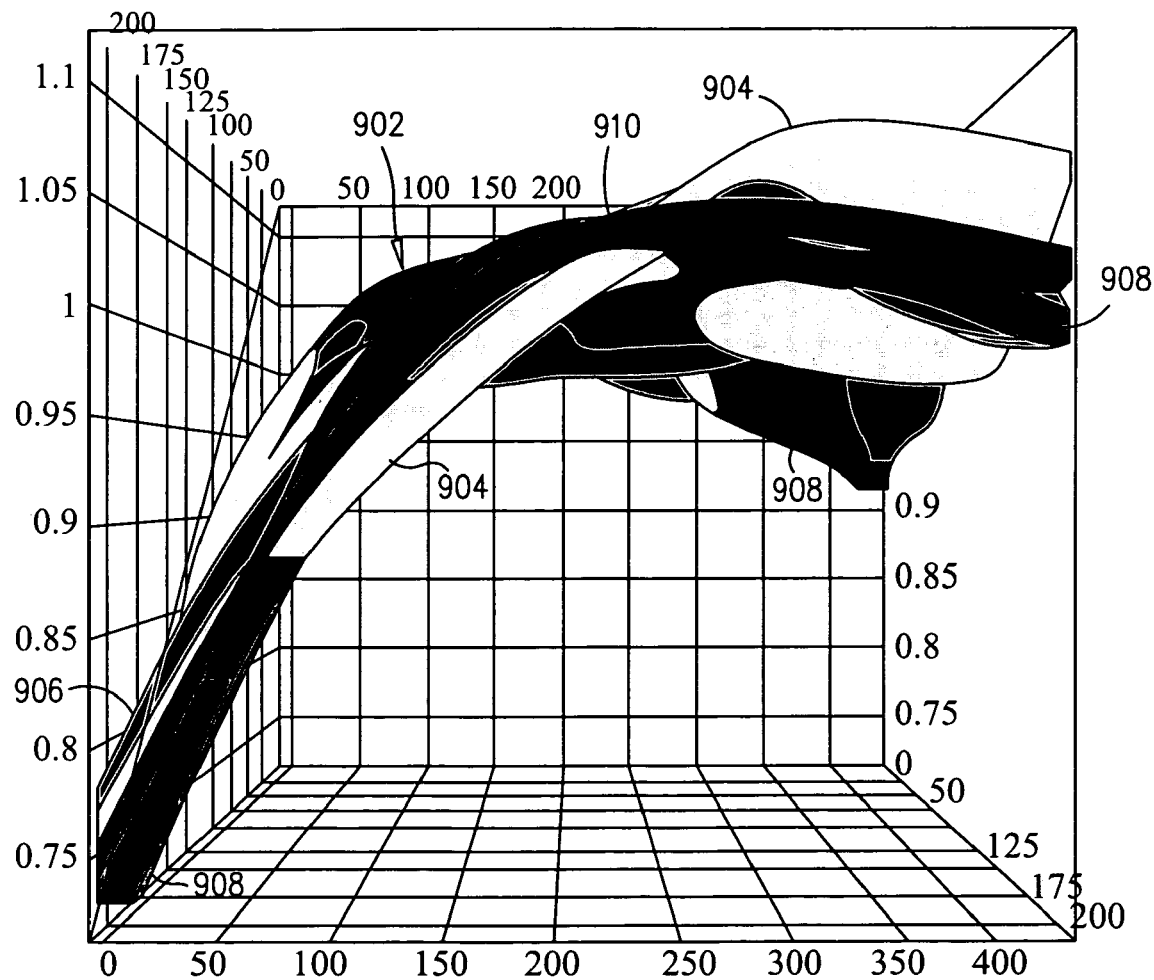
FIG. 10A is a scatter plot showing a surface fit to background subtracted signals from a red channel for all probes on the same array referred to in FIGS. 9A-9B.
Figure 10B:
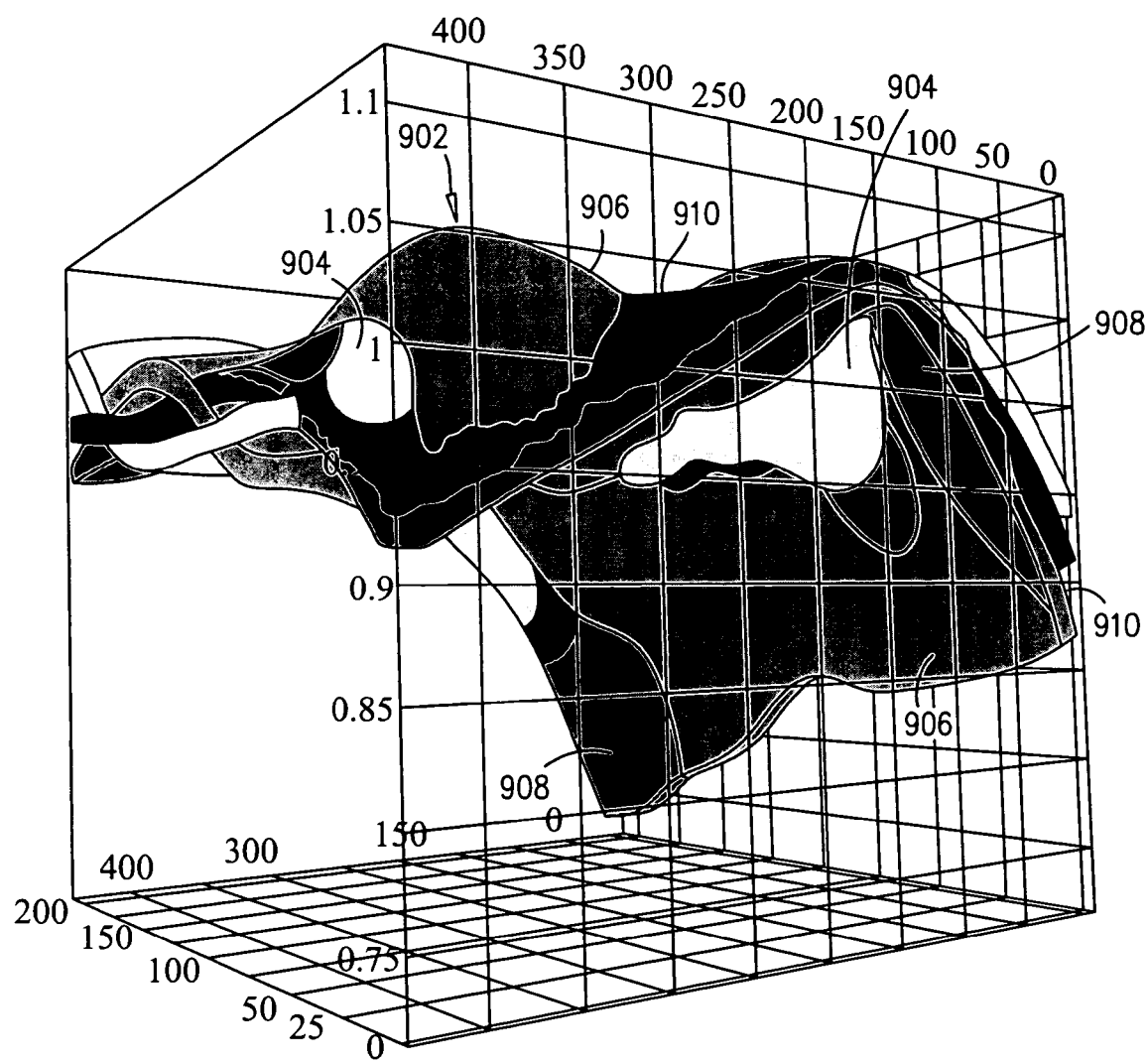
FIG. 10B is the plot of FIG. 10A having been rotated about axis 1 by 180 degrees.

FIG. 10A is a scatter plot 902 showing the surface fit to the background subtracted signals from the red channel for all probes on the array. The lightest color portion (grey) 904 is a plot of the surface fitted to the background-subtracted signals from the bin containing the highest signal intensity values, the olive drab colored portions 906 plot the surface fitted to the background subtracted signals from the bin containing the medium signal intensity values, the green colored portions 908 plot the surface fitted to the background subtracted signals from the bin containing the dimmest, or lowest intensity signals, and the blue portions 910 plot the fit averaging of each sequence to the average value of the signal intensities of the replicates of that sequence. Signal values were plotted in the same way as described with regard to FIG. 9A. The fitted data after processing the binned average value data and fitting it to the background subtracted signals is shown as described. FIG. 10B shows the same data which has been rotated by one hundred eighty degrees about the vertical (intensity) axis.

From the results of fitting shown in FIGS. 9A-10B, it was concluded that the shape of the gradient is the same across intensities, and therefore does not depend on the intensity range, i.e., there is not a multiplicative trend with this array, since the shape of the surface for each corresponding bin (where each bin represented a different intensity range) showed substantially the same gradient contours as can be seen in FIGS. 9A-10B. The average absolute values of the differences between the different normalized surfaces (at corresponding locations) were compared to determine similarity. These differences were well below the average variability between the background-subtracted signal intensities between replicate features and thus the replicate averaging technique was considered to be acceptable for use in surface fitting as described.

The difference for a surface fit between the front left row of the array (i.e., row 0, column 100) and the middle of the array is about 35% (0.75 to 1.1) This is true for all of the surface fits to the different sets of signal intensity values. Therefore, the size of the difference between the highest and lowest part of the surfaces is around 35%. By contrast, the difference between the different surface fits that were calculated at any given location tend to be less than about 5%. Therefore, it was concluded that the different surface fits give substantially the same surface (i.e., shape of the surfaces were much more similar than they were different).

Example 2

As noted above, many arrays will not be designed with thirty replicates of each probe, and some may even have only one replicate for each sequence. A test was therefore run to determine whether fitting according to the described techniques is viable for arrays that do not have multiple replicates of each probe. The most restrictive case was exemplified, i.e., where only one replicate (i.e., one feature) is provided on the array for each sequence and therefore all signal values need to be considered in the calculations. Thus, all the signal data was used, although the same oversampled array was scanned to supply the signals, for comparison purposes with the results from Example 1, except for those signals that were determined to be saturated or from a non-uniform feature. Filtering to remove "dim features" was not performed in this example. After excluding all saturated and non-uniform features, the intensities of the remaining signals were transformed to log space and then fitted to a surface approximation calculated by a second order polynomial algorithm, to which the background subtracted signals of all features were then fitted in the same manner as described in Example 1, and according to the disclosure herein, but where all the signals (except saturated, non-uniform and negative controls) were inputted for fitting, rather than average values.

Figure 11A:
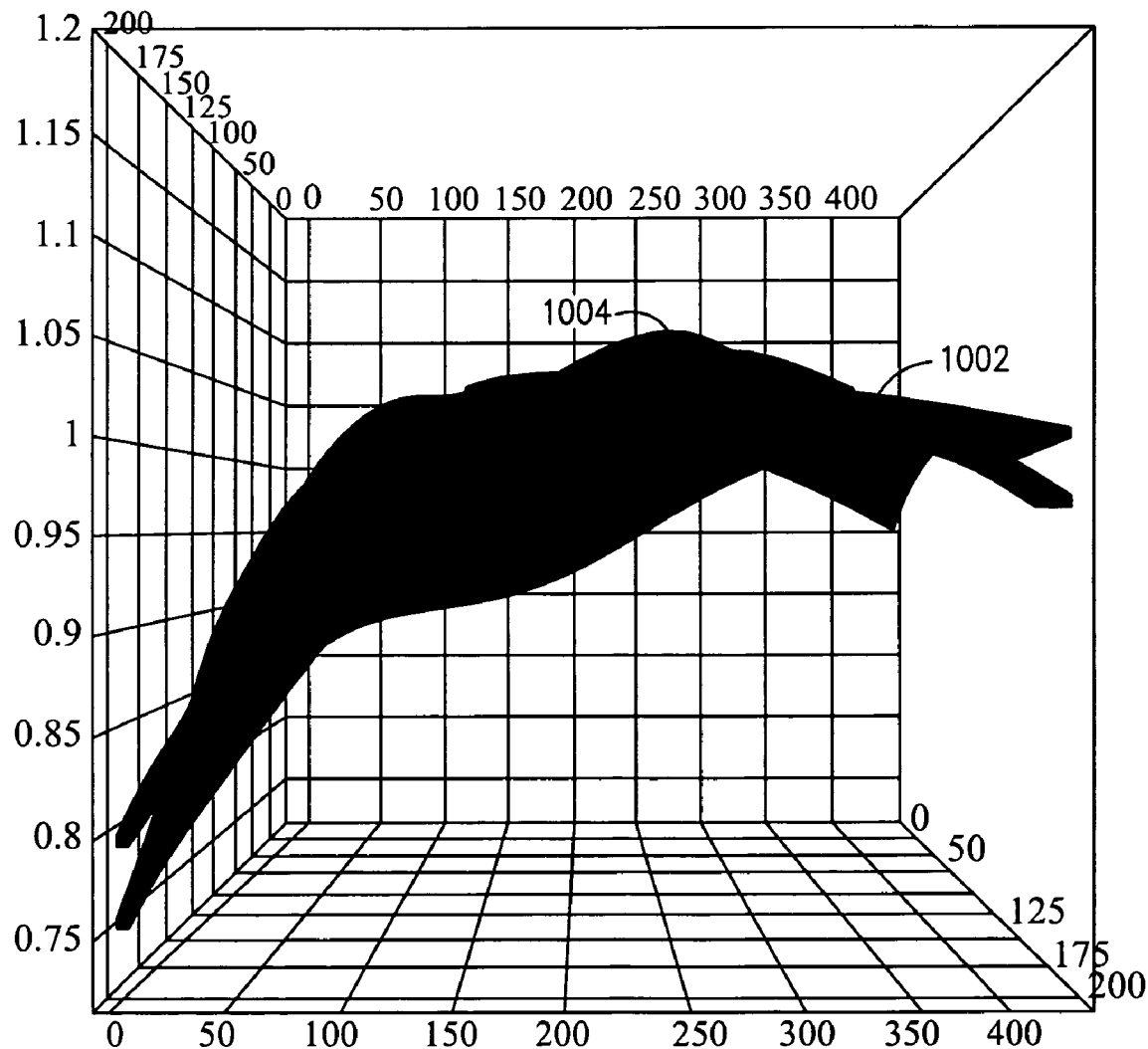
FIG. 11A shows scatter plots of signals processed from a green channel of probes on an array as described in Example 2.

FIG. 11A shows scatter plots of surface fits to the signals processed from the green channel in Example 2, compared to the results of Example 1. The red color plotted fit surface 1002 is the surface resulting when each feature was normalized to the replicate average intensity value (i.e., the fit from Example 1). The blue color plotted fit surface 1004 is the surface generated by the surface fit to the log of all the background-subtracted signal data values (except those filtered out, as mentioned above), and normalized to the surface average in a manner as described above (i.e., by subtracting the surface average value from the signal intensity value of every feature to make the average value of the normalized surface fit equal to zero), and then reverse log-transforming the data (i.e., the fit performed in Example 2).

Figure 11B:
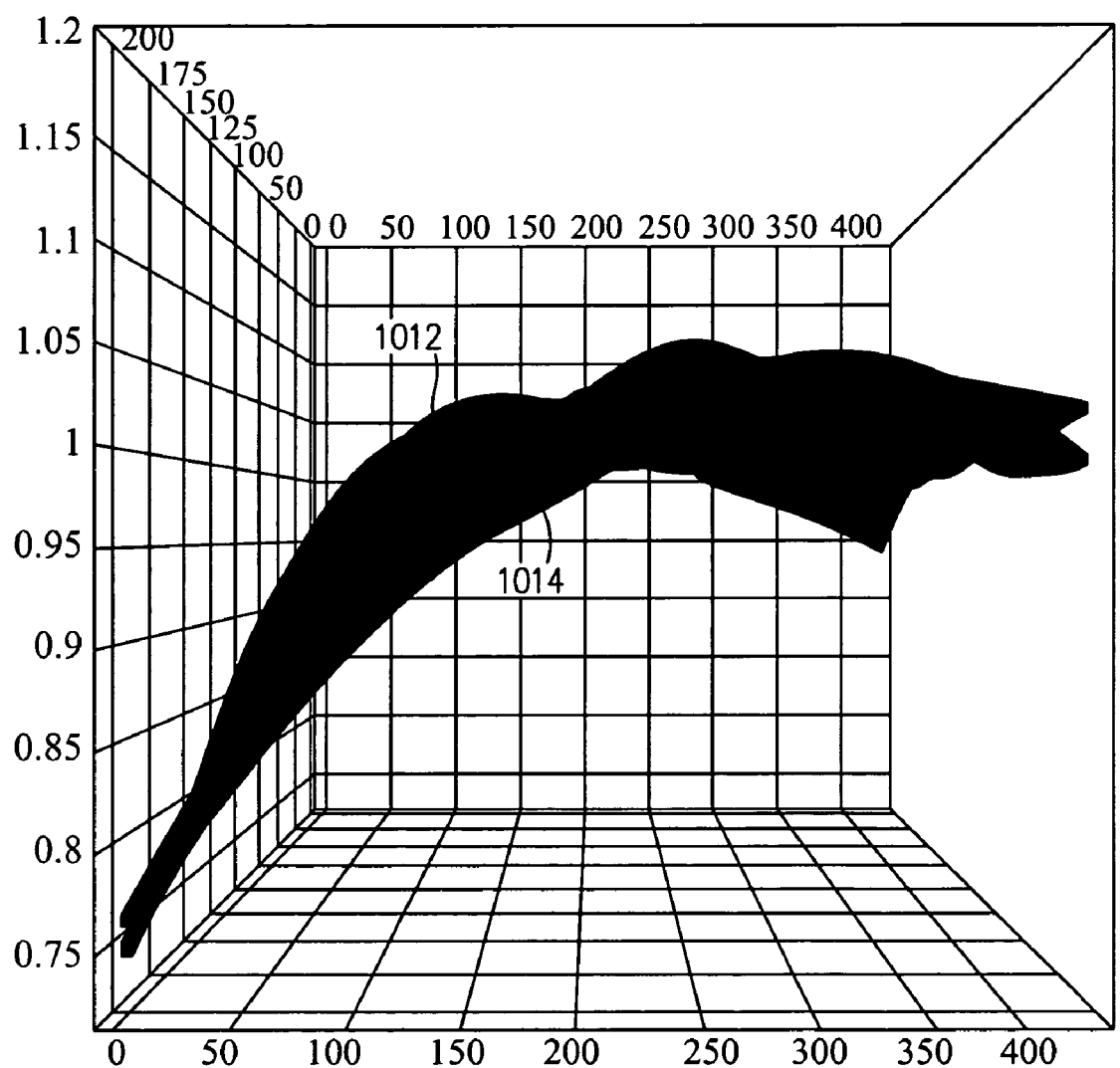
FIG. 11B shows scatter plots of signals processed from a red channel of probes on an array as described in Example 2.

FIG. 11B shows scatter plots of surface fits to the signals processed from the red channel in Example 2, compared to the results of Example 1. The red fit surface 1012 is the surface resulting when each feature was normalized to the replicate average intensity value (i.e., the fit described in Example 1). The blue surface 1014 is the surface fit to the log of the background-subtracted signals of all the signal data values (except those filtered out, as mentioned above) after normalization to a surface average in a manner as described above (i.e., by subtracting the surface average value from every point (feature intensity value) to make the average value of the normalized surface fit equal to zero), and then reverse log-transforming the data (i.e., the fit described in Example 2).

From the visual comparison of the fit surfaces 1002 to 1004 and 1012 to 1014, respectively, it can be observed that the use of all the signal data at once in the log space transformation used to fit the surface produces results that are nearly the same as those produced using averages of replicates when replicates are available.

Figure 12:
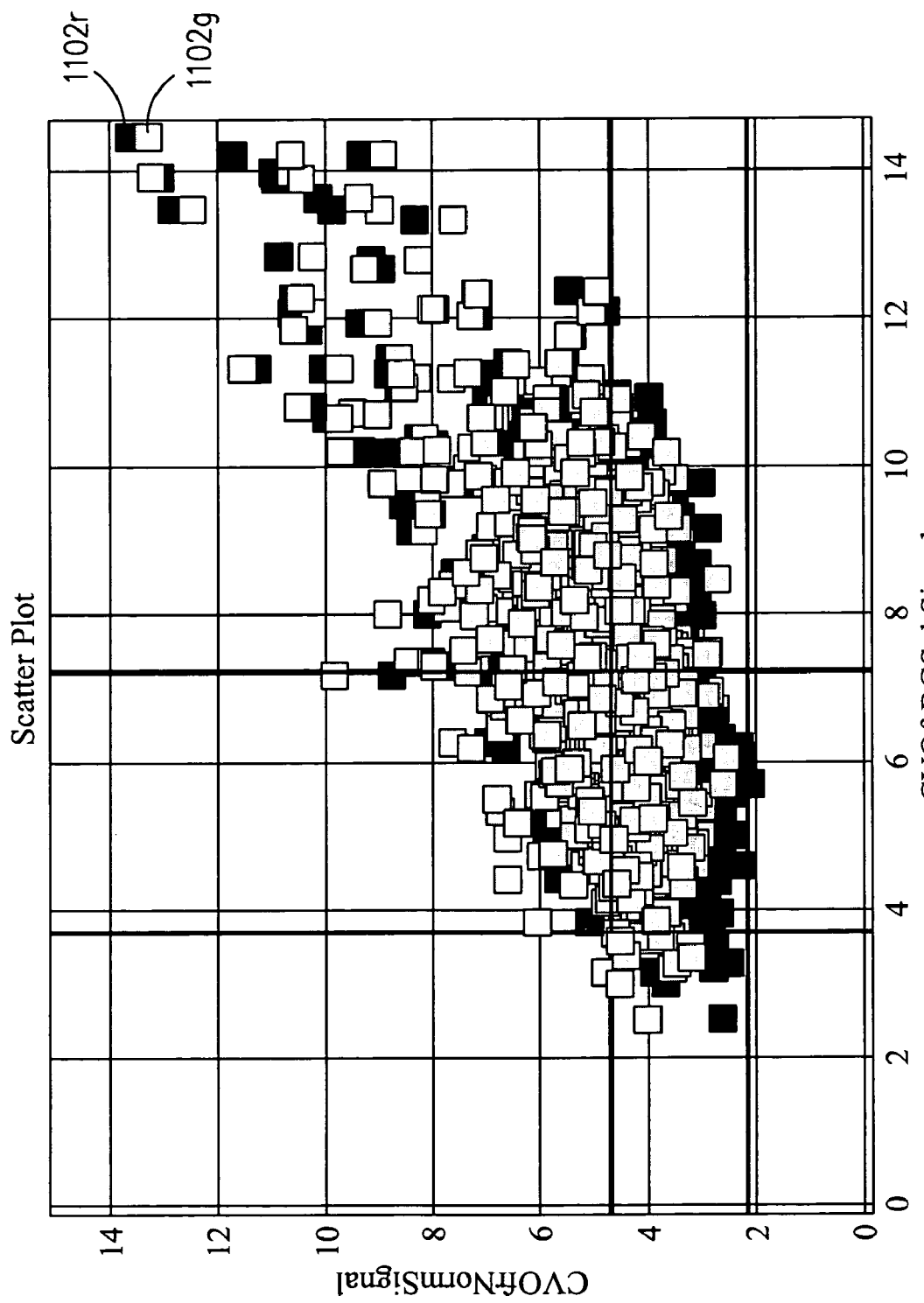
FIG. 12 plots coefficients of variance (CV) of replicates within an array for the red channel, wherein the red blocks represent signal values normalized to a surface approximated from replicate average intensity values.

FIG. 12 plots coefficients of variation (CV) of replicates within the array for the red channel, wherein the red blocks 1102r represent signal values normalized to a surface approximated from replicate average intensity values. That is, the signal values from the features of the array were normalized by dividing by the values from the surface fit (calculation of surface approximation) that was performed with replicate average intensity values used as input to calculate the surface approximation. The gray blocks 1102g represent the signal values where all signal values (except saturated, non-uniform) were used in log space as inputs for the surface fit, and then normalized, as described in Example 2. It can be observed that the results from the two different methods give comparable results, since the CV values are very close to one another and overlapping.

Accordingly, after performing the above two examples and analysis thereof, it was concluded that the surface fitting of all feature intensity signals (after background subtracting and removing additive noise, as well as optionally filtering out dim signals) in log space and then normalizing the surface to the average value of the surface fit, and then de-trending the signal intensity data by dividing it by the normalized surface values at corresponding locations, provides comparable results to the use of oversampled feature intensity signals where normalized, average values are used to the replicates of each feature.

Thus it is acceptable to use all of the feature intensity signals from dim to bright according to fit the surface according to the present techniques because the shape of the multiplicative trend that may be present is the same regardless of signal range. Further, it is acceptable to use all of the feature intensity signals from dim to bright according to fit the surface according to the present techniques, as an alternative to the methods that use normalized, average replicate values, as the resulting surface fits are very comparable and acceptable. Advantageously, therefore, the current techniques can be applied even to arrays that do not contain replicate features.

The use of a second order polynomial fit was chosen for the examples, rather than using Loess, as it was faster to calculate (i.e., taking seconds for an array containing 44,000 features, as opposed to minutes required for calculating the same using Loess). Because of this speed advantage, a moving average window (e.g., 2×2 features window was not needed. The second order polynomial fit was also found to be more accurate as it better fit the actual shape of the surfaces, compared to fitting using Loess, and was less influenced by noise. The use of the second order polynomial fits also provided superior improvement in the coefficients of variation between replicate features within and between arrays.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

The invention claimed is:

1. A system for removing trends in signal intensity values from features on a chemical array, said system comprising:
   a processor;
   one or more sequences of instructions for removing trends, wherein execution of said one or more sequences of instructions by said processor causes said processor to perform operations comprising:
   inputting signal intensity values from all features on the array except signal intensity values from features removed by filtering to remove at least features having the lowest signal intensity values and control features;
   calculating a log transform of each signal intensity value inputted from said all features on the array except signal intensity values from features removed by filtering to remove at least features having the lowest signal intensity values and control features, to provide log signal intensity values;
   calculating a surface approximation of the log signal intensity values;
   normalizing surface fit values on the calculated surface approximation in locations corresponding to locations of the features on the array from which signal intensity values were inputted;
   calculating a reverse log transform of the normalized surface fit values; and
   de-trending the inputted signal intensity values as a function of the normalized surface values in locations corresponding to the locations of the features from which the signal intensity values were inputted; and
   an interface through which de-trended signal intensity values are outputtable.

2. The system of claim 1, wherein the storage device stores a second order polynomial algorithm for calculating the surface approximation.

3. The system of claim 1, wherein the storage device stores a locally weighted, least squares regression algorithm for calculating the surface approximation.

4. The system of claim 1, wherein said features removed by filtering further comprise at least one of saturated features and non-uniform features.

5. A system for removing trends in signal intensity values from features on a chemical array, said system comprising:
   a processor;
   one or more sequences of instructions for removing trends, wherein execution of said one or more sequences of instructions by said processor causes said processor to perform operations comprising:

inputting signal intensity values from features on the chemical array;

segmenting the array into local areas of predetermined dimensions, each said local area comprising multiple features;

calculating an average signal intensity value for each local area from the intensity values inputted of features within that local area;

calculating a surface approximation of the average signal intensity values versus locations on the array of the centers of the local areas from which the average signal intensity values were calculated, normalizing surface values of the surface approximation at locations corresponding to the locations of features on the array; and dividing the signal intensity values from the features by the normalized surface values at locations corresponding to the locations of the features on the array to provide trend-corrected signal intensity values; and an interface through which the trend-corrected signal intensity values are outputtable.

6. The system of claim 5, further comprising a chemical array having an oversampled design that includes at least ten replicates of each feature designed to measure a sample.

7. The system of claim 6, wherein the chemical array includes at least thirty replicates of each feature designed to measure a sample.

8. A system for removing trends in signal intensity values from features on a chemical array, said system comprising:

a processor;

one or more sequences of instructions for removing trends, wherein execution of said one or more sequences of instructions by said processor causes said processor to perform operations comprising:

inputting signal intensity values from features on the chemical array, wherein the chemical array contains replicates of features designed to measure a sample;

for each feature, averaging signal intensity values for all replicates of that feature;

for each feature, normalizing the intensity values of all replicates of that feature to a predetermined intensity value;

calculating a surface approximation of the averaged, normalized intensity values versus locations on the array of the replicates from which the averaged, normalized intensity values were calculated; normalizing surface values of the surface approximation at locations corresponding to the locations of features on the array; and dividing the signal intensity values from the features by the normalized surface values at locations corresponding to the locations of the features on the array to provide trend-corrected signal intensity values; and an interface through which the trend-corrected signal intensity values are outputtable.

* * * * *